United States Patent
Shener et al.

(10) Patent No.: US 7,604,610 B2
(45) Date of Patent: Oct. 20, 2009

(54) SURGICAL FLUID MANAGEMENT

(75) Inventors: Cemal Shener, Woburn, MA (US); Kenneth W. Krause, Sandown, NH (US); Petter Hedstrom, Haverhill, MA (US); Brian J. Loreth, Braintree, MA (US)

(73) Assignee: Smith & Nephew, Inc., Memphis, TN (US)

( * ) Notice: Subject to any disclaimer, the term of this patent is extended or adjusted under 35 U.S.C. 154(b) by 293 days.

(21) Appl. No.: 11/423,899

(22) Filed: Jun. 13, 2006

(65) Prior Publication Data

US 2007/0078370 A1    Apr. 5, 2007

Related U.S. Application Data

(60) Provisional application No. 60/689,540, filed on Jun. 13, 2005.

(51) Int. Cl.
*A61M 31/00* (2006.01)
(52) U.S. Cl. .............. 604/67; 604/66; 604/65
(58) Field of Classification Search ............ 604/65–67, 604/131, 151; 700/42
See application file for complete search history.

(56) References Cited

U.S. PATENT DOCUMENTS

| | | | |
|---|---|---|---|
| 3,900,022 A | 8/1975 | Widran | |
| 4,482,346 A * | 11/1984 | Reinicke | 604/152 |
| 4,650,462 A | 3/1987 | DeSatnick et al. | |
| 4,650,562 A | 3/1987 | DeSatnick et al. | |
| 4,820,265 A | 4/1989 | DeSatnick et al. | |
| 5,176,629 A | 1/1993 | Kullas et al. | |
| 5,322,506 A | 6/1994 | Kullas | |
| 5,344,292 A | 9/1994 | Rabenau et al. | |
| 5,464,391 A | 11/1995 | DeVale | |
| 5,520,638 A | 5/1996 | O'Quinn et al. | |
| 5,536,254 A | 7/1996 | McVay | |
| 5,630,798 A | 5/1997 | Beiser et al. | |
| 5,630,799 A | 5/1997 | Beiser et al. | |
| 5,643,203 A | 7/1997 | Beiser et al. | |
| 5,643,302 A | 7/1997 | Beiser et al. | |
| 5,662,611 A | 9/1997 | Beiser et al. | |
| 5,755,691 A | 5/1998 | Hilborne | |
| 5,800,383 A | 9/1998 | Chandler et al. | |
| 5,830,180 A | 11/1998 | Chandler et al. | |
| 5,840,060 A | 11/1998 | Beiser et al. | |
| 5,882,339 A | 3/1999 | Beiser et al. | |
| 5,931,808 A | 8/1999 | Pike | |
| 6,024,720 A | 2/2000 | Chandler et al. | |

(Continued)

FOREIGN PATENT DOCUMENTS

EP    0 278 188 A2    8/1988

(Continued)

*Primary Examiner*—Nicholas D Lucchesi
*Assistant Examiner*—Rebecca E Eisenberg
(74) *Attorney, Agent, or Firm*—Fish & Richardson P.C.

(57) ABSTRACT

A fluid flow device includes a housing configured to releasably mate with a surgical control unit for controlling fluid flow during a surgical procedure. First and second ports measure fluid pressure within a fluid path provided within the housing. The fluid flow device includes a restrictor for restricting fluid flow at a restriction location along the fluid path. The first port is located upstream of the restriction location and the second port is located downstream of the restriction location. A fluid pump is provided within the housing.

25 Claims, 16 Drawing Sheets

U.S. PATENT DOCUMENTS

| | | | |
|---|---|---|---|
| 7,291,126 B2 * | 11/2007 | Shekalim | 604/67 |
| 2002/0085952 A1 * | 7/2002 | Ellingboe et al. | 422/45 |

FOREIGN PATENT DOCUMENTS

| | | |
|---|---|---|
| EP | 0278188 | 8/1988 |
| EP | 0529902 | 8/1992 |
| WO | WO 84/02473 | 7/1984 |
| WO | 98/02205 | 1/1998 |
| WO | 00/12150 | 8/1999 |
| WO | 00/12150 | 3/2000 |
| WO | WO 00/28890 | 5/2000 |

\* cited by examiner

SURGICAL FLUID MANAGEMENT

CROSS-REFERENCE TO RELATED APPLICATIONS

This application claims priority under 35 U.S.C. § 119 to U.S. Provisional Application No. 60/689,540, filed on Jun. 13, 2005. The entire contents of which are incorporated by reference herein.

BACKGROUND

This description relates to fluid management for surgical procedures.

In an endoscopic procedure, such as arthroscopic surgery, a fluid management system is used to supply fluid to a body cavity. The fluid is delivered to a joint cavity to provide access and visibility to the surgeon performing a surgical procedure within the cavity. The fluid is used to flush the joint cavity of blood and debris, and/or to maintain a reasonable level of joint distension.

SUMMARY

In one general aspect, a fluid flow device includes a housing configured to releasably mate with a surgical control unit for controlling fluid flow during a surgical procedure. The flow device includes a fluid path within the housing, and first and second ports for measuring fluid pressure within the fluid path. A restrictor restricts fluid flow at a restriction location along the fluid path. The first port is located upstream of the restriction location and the second port is located downstream of the restriction location. The flow device includes a fluid pump within the housing.

Implementations of this aspect may include one or more of the following features. For example, the restrictor includes a region of decreased cross-sectional area along the fluid path. The ports are openings defined in a wall of the housing.

The flow device includes a flexible membrane covering the first port and a flexible membrane covering the second port.

The pump includes a non-contact, magnetic coupling configured to be operatively driven by a motor external to the housing.

The flow device includes a second fluid path within the housing.

The flow device includes a valve configured to selectively control fluid flow through the second fluid path.

Day-tubing is operatively connected to the housing. The day-tubing includes a valve for limiting backflow.

The flow device includes the surgical control unit. The surgical control unit includes a first pressure sensor and a second pressure sensor. The sensors align with the ports when the housing is mated with the surgical control unit. The surgical control unit defines a slot for receiving the housing. The slot includes a guide track and the housing includes one or more protrusions configured to matingly engage the guide track. The guide track includes a linear track section and an angled track section.

The flow device includes a valve configured to impart a pulsating action to a fluid conduit within the housing.

The surgical control unit includes a processor configured to selectively control pump speed based on a measured pressure drop across the flow restrictor. The processor is configured to selectively control pump speed based on a calculated flow rate, a setpoint surgical site pressure, and a calculated surgical site pressure. The processor is operatively connected with a proportional-integral-derivative controller configured to provide closed-loop feedback with respect to a comparison between the setpoint surgical site pressure and the calculated surgical site pressure.

The surgical control unit is configured to control pump outlet pressure (P2), flow rate (Q) and pump speed (RPM) based on a three-dimensional system model defined by the function RPM=f(P2, Q). The controller is configured to provided open-loop feed forward control with respect to a comparison between the setpoint surgical site pressure and the calculated surgical site pressure.

In another general aspect, a method for controlling fluid pressure within a body cavity includes pumping fluid to the body cavity through a flow restrictor located between the body cavity and a fluid pump, measuring a pressure change across the flow restrictor, calculating the fluid pressure within the body cavity based on the measured pressure change, and controlling the fluid flow to the body cavity based on the calculated fluid pressure.

Implementations of this aspect may include one or more of the following features. For example, the method includes setting a setpoint body cavity pressure, comparing the calculated fluid pressure in the body cavity with the setpoint body cavity pressure, and adjusting pump operating speed based on the comparison. Pump outlet pressure (P2), flow rate (Q) and pump speed (RPM) are controlled based on a three-dimensional system model defined by the function RPM=f(P2, Q). Open-loop feed forward control is provided based on the comparison and closed loop feedback control is provided based on pump speed.

In another general aspect, a computer-readable recording medium stores computer-executable program codes configured to cause a computer to perform the above method.

In another general aspect, a fluid flow device for controlling pressure in a body cavity may include one or more of the following features. For example, the pump is a centrifugal pump. The first pressure sensor and the second pressure sensor are transducers adjacent to the cassette slot and aligned with the first and the second ports when the housing is operatively received within the slot. The surgical control unit includes a sensing device that detects a housing operatively received within the housing slot. The sensing device identifies the housing.

In another general aspect, a pump cassette is capable of releasably mating with a surgical control unit that defines a cassette receiving slot with a guide track and has first and second pressure transducers. The pump cassette includes a housing having a protrusion configured and arranged to mate with the guide track during introduction into and final placement within the slot such that the housing is spaced from the pressure transducers during introduction into the slot and contacts the pressure transducers when in final placement within the slot.

Implementations of this aspect may include one or more of the following features. For example, the pump cassette includes first and second ports positioned for alignment with the first and second pressure transducers when the cassette is in final placement within the slot.

In another general aspect, a method of mating a pump cassette to a surgical control unit, the surgical control unit defining a cassette receiving slot with a guide track and having first and second pressure transducers includes aligning a protrusion on the cassette with the guide track and pushing the cassette into the guide track such that the cassette moves from a position spaced from the pressure transducers during introduction into the slot to a final placement in contact with the pressure transducers.

In another general aspect, an apparatus for controlling fluid pressure within a body cavity includes means for pumping fluid to the body cavity through a flow restrictor located between the body cavity and a fluid pump, means for measuring a pressure change across the flow restrictor, means for calculating the fluid pressure within the body cavity based on the measured pressure change, and means for controlling the fluid flow to the body cavity based on the calculated fluid pressure.

One or more of the foregoing aspects provides one or more of the following advantages. The fluid management system increases functionality, ease of operation, and reliable monitoring and control of system parameters, such as joint pressure within a body cavity. For example, joint pressure can be maintained at a setpoint pressure to achieve adequate joint distension and/or to avoid overpressurizing a joint cavity. Joint pressure can be controlled to substantially equal a target setpoint pressure by varying fluid flow device parameters, such as by varying pump speed independent of flow rate. The fluid management system can be used to reliably and automatically recognize instrument and disposable pump cassette types to establish system pressure impedances. The use of the aforementioned disposable, arthroscopic pump in the fluid management system provides outflow control that limits tissue clogging in the fluid flow path(s). The system is compatible with a wide range of arthroscopic instruments, cannulas and/or tubing configurations without requiring manual calibration and/or calculation of pressure losses. The system permits the recognition of adequate fluid bag heights, accurate pressure loss measurement, flow rate and pump speed control and/or calculation.

Other features, objects, and advantages will be apparent from the description and drawings, and from the claims.

DETAILED DESCRIPTION

Figure 1A:
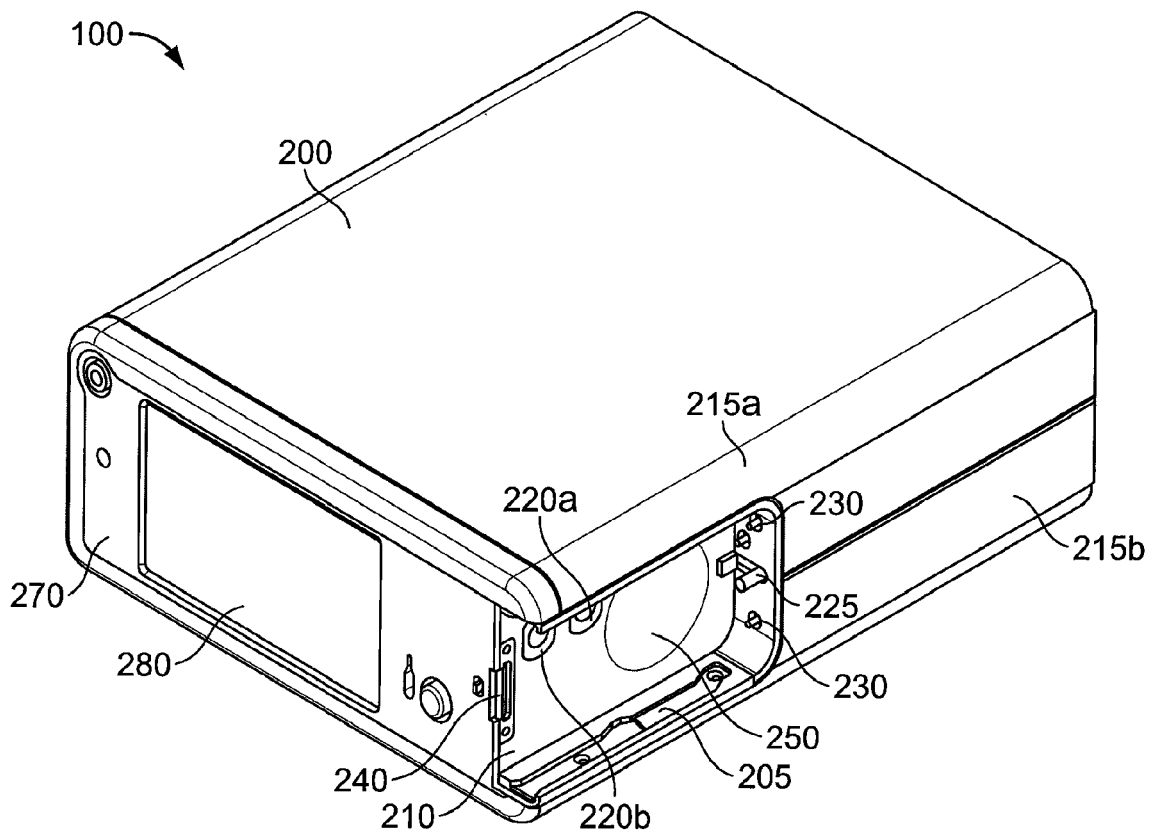
FIGS. 1A and 1B are illustrations of a fluid management system including a pump control unit and a pump cassette.
Figure 1B:
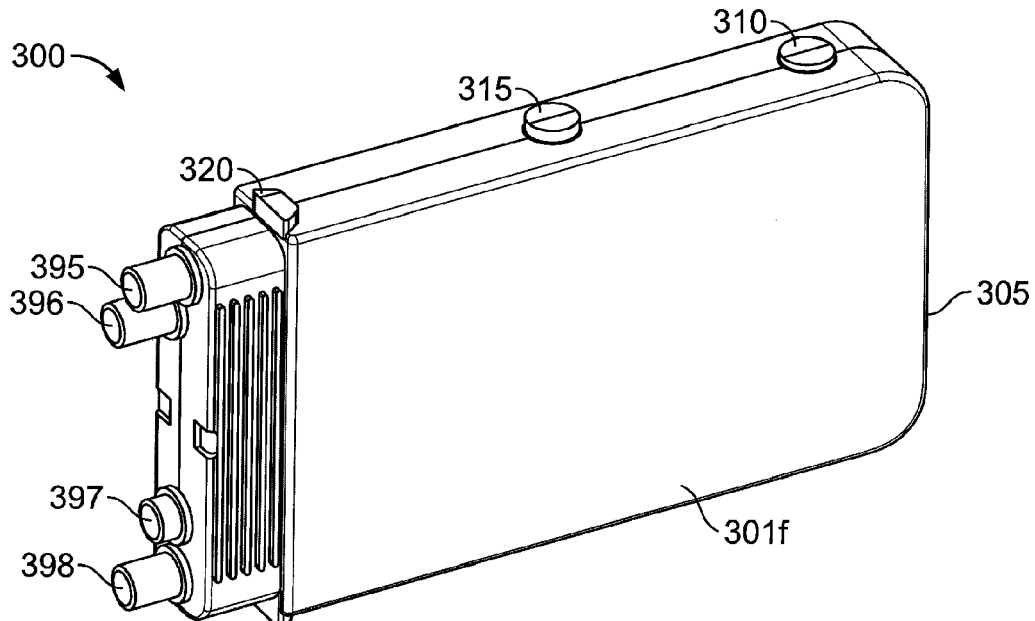

A fluid management system 100 includes a pump control unit 200 (FIG. 1A) and a disposable pump cassette 300 (FIG. 1B). The fluid management system 100 is used in an endoscopic procedure, such as arthroscopic surgery, to supply pressurized fluid to a body cavity. The fluid is delivered to produce a substantially constant predetermined pressure level within the joint cavity. Joint cavity pressure is controlled by the system 100 by varying pump speed, e.g., independent of the rate of flow Q, to maintain a level of joint distension, to provide sufficient access and visibility to the surgeon, and/or to flush the cavity of blood and debris. As the demand for flow Q fluctuates throughout a surgical procedure, the system 100 automatically adjusts the control unit 100 to deliver the proper flow rate and to maintain a desired joint pressure in the cavity.

The pump control unit 200 includes a housing 215a, 215b defining a generally rectangular-shaped pump cassette slot 210 for operatively receiving pump cassette 300, which is removably slid into slot 210. As discussed below, the cassette slot 210 and the pump cassette 300 are configured such that the cassette is capable of being inserted into the slot 210 only in a single direction and orientation. The control unit housing 215a, 215b includes an upper section 215a and a lower section 215b removably secured to each other to permit access to an interior of the control unit 200.

Figure 2A:
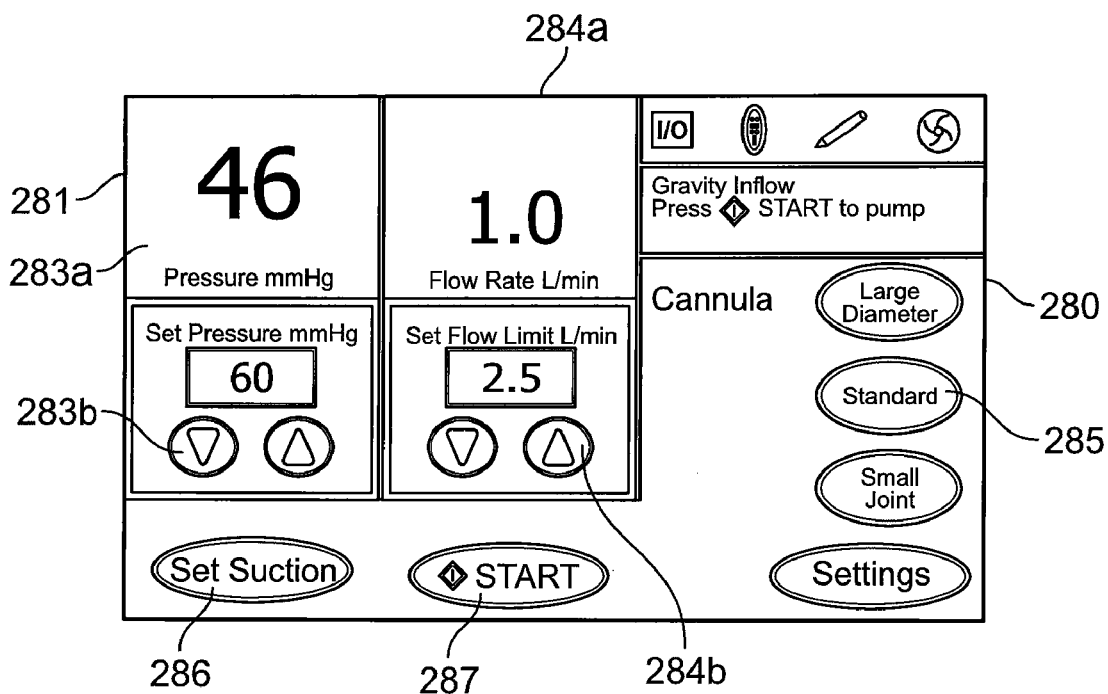
FIGS. 2A-2B are exemplary screenshots from a display of the pump control unit of FIG. 1A.
Figure 2B:
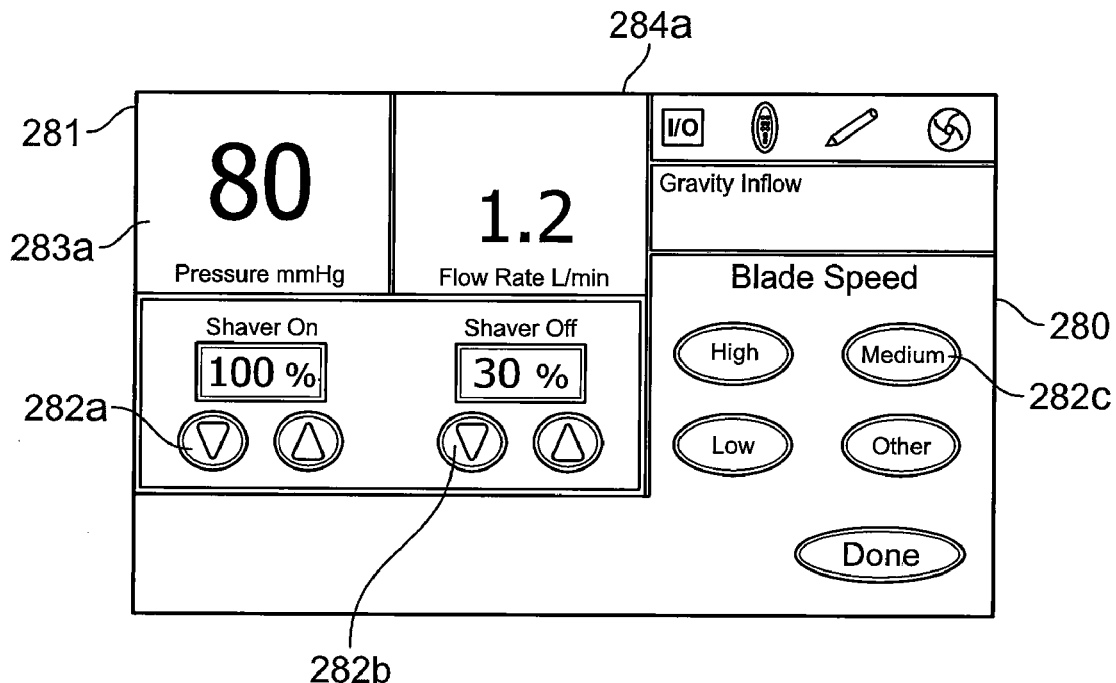

Referring to FIGS. 2A-2B, the pump control unit 200 includes a front surface 270 having a display 280 providing a graphical user interface 281. The graphical user interface 281 is, for example, a touch-screen activated interface that permits a user to selectively control or monitor various system parameters. For example, referring to FIG. 2A, an initial screen permits the user to set a target joint pressure 283b, to set a flow limit 284b, and to select arthroscopic instrument settings 285, such as large diameter, standard or small joint cannula settings. The initial screen also provides the user with the ability to select and set suction level 286 and joint cavity pressure 283b, to start or deactivate the pump 287, and/or to monitor measured parameters, such as joint pressure 283a and flow rate 284a. Referring to FIG. 2B, a subsequent screen permits the user to adjust settings relating to a surgical procedure, such as setting arthroscopic instrument settings. For example, the control unit 200 is capable of being operated with a shaver system, such as a Dyonics Power Shaver System, part number 7205357 manufactured by Smith & Nephew, Inc. The shaver system may provide a variety of shavers in different sizes, such as 2.0 mm, 2.9 mm, and 3.5 mini blades and burrs for joint applications. In addition, the shaver system can include a blade recognition feature that automatically senses the type of shaver blade and sets the system to a programmed speed range for optimal performance and safety. Alternatively, the user can select the blade speed 282c. Upon setting the blade speed, the user can also designate shaver suction settings on the control unit 200 depending on whether the shaver is on 282a, or off 282b.

Figure 3:
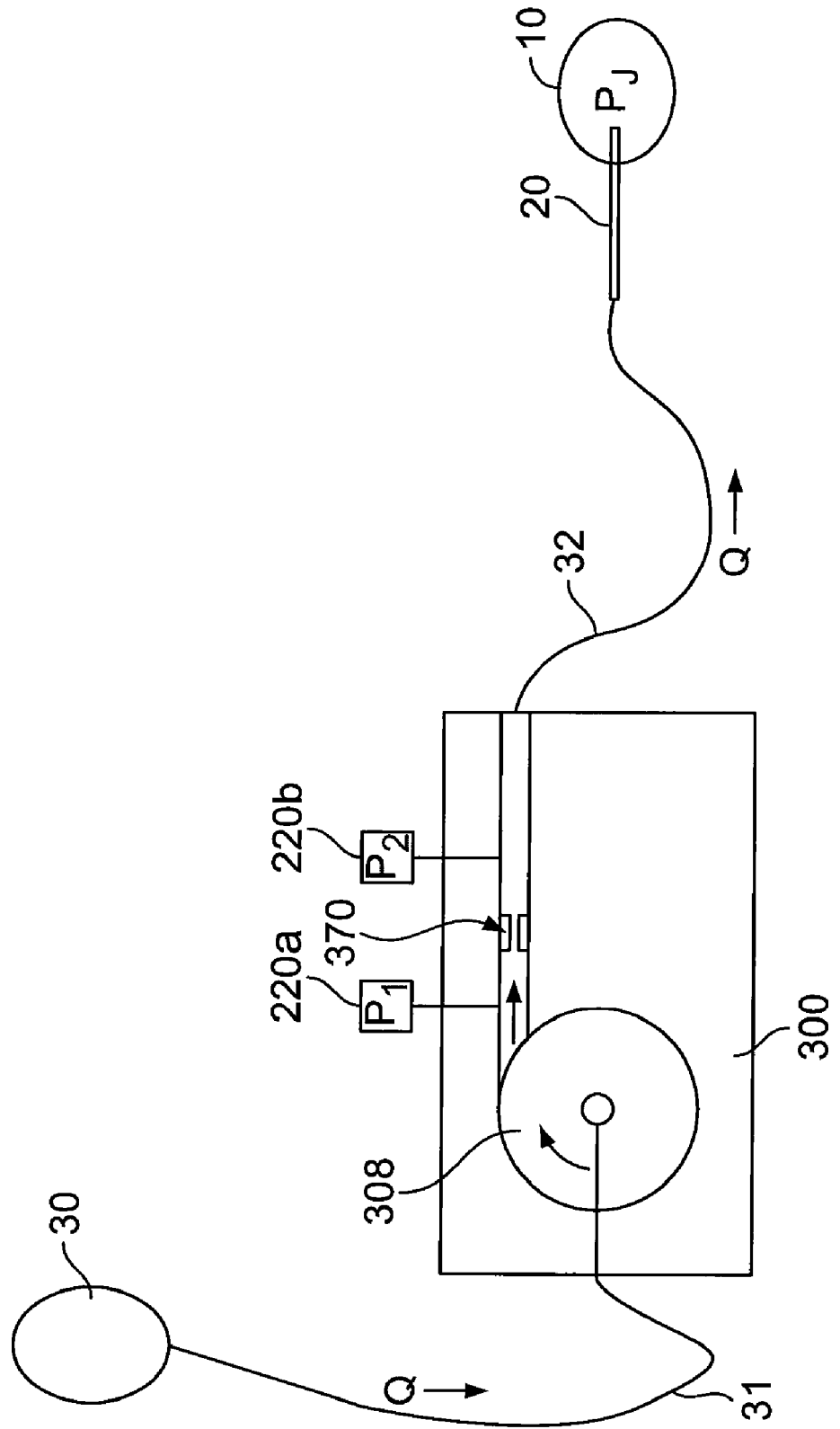
FIG. 3 is a schematic of the fluid management system in use during an endoscopic surgical procedure.

Referring to FIGS. 1A-1B and 3, the pump control unit 200 includes a pair of pressure transducers 220a, 220b for measuring respective pressures P1, P2 across a flow restriction 370 within the pump cassette 300. In use, a fluid bag 30 is operatively connected through surgical tubing 31 with the pump cassette 300 for supplying fluid to a supply fluid inlet tubing connection 397 (FIG. 1B). The pump cassette 300 includes a centrifugal pump 308 that supplies pressurized fluid at a flow rate Q to joint cavity 10 through an outlet tubing connection 396 (FIG. 1B), a discharge tubing 32 and a cannula 20. The pressure transducers 220a, 220b measure the pressure drop across the flow restriction 370 to derive the flow rate Q. The flow rate Q, along with various system parameters discussed below, can be used to generate a transfer function or three-dimensional mathematical model that is used to control flow rate to and fluid pressure within the joint cavity 10.

To determine the flow rate to and fluid pressure in the joint cavity 10, the impedance or pressure drop $\Delta P_R$ across the cannula 20, tubing 32, and any fittings (not shown) between the joint cavity 10 and transducer 220b, which represents the pressure loss between the transducer 220b and a distal end of the cannula 20, should be accounted for. The impedance may be empirically calculated as a continuous function in the form of $\Delta P_R = f(Q)$:

$$\Delta P_R = a_R Q^2 + b_R Q \quad \text{Eq. 1}$$

The coefficients $a_R$ and $b_R$ of Equation 1 can be derived empirically for each type of instrument configuration used with the system 100, and stored within the control unit 200. For example, three families of impedance equations have been quantified that represent a 'low' flow, a 'medium' flow and a 'high' flow set of instruments. For example, a low flow instrument configuration includes a Smith & Nephew, Inc. catalog reference numbers 3672 and 7205682 (2.9 mm OD cannula with 2.7 mm OD arthroscope), a medium flow instrument configuration includes Smith & Nephew, Inc. catalog reference numbers 4492 and 3894 (5.8 mm OD rotatable cannula with 4 mm OD arthroscope), and a high flow instrument configuration includes Smith & Nephew, Inc. catalog reference numbers 4537 and 3894 (6 mm OD cannula with 4 mm OD arthroscope). The arthroscope is inserted into the cannula and the annular area between the outer diameter of the arthroscope and the inner diameter of the cannula defines the flow area. The following equations represent these three types of instruments:

$$\Delta P_{RL} = a_{RL} Q^2 + b_{RL} Q \text{ (low flow)} \quad \text{Eq. 2}$$

$$\Delta P_{RM} = a_{RM} Q^2 + b_{RM} Q \text{ (medium flow)} \quad \text{Eq. 3}$$

$$\Delta P_{RH} = a_{RH} Q^2 + b_{RH} Q \text{ (high flow)} \quad \text{Eq. 4}$$

In addition, when a multiple-use tube set, e.g., a day-tube set is used in the system, the impedance of the day tubing set is also factored into determining the system impedance with Equation 5. The multiple-use tube set can include a backflow preventing check valve that limits contamination, and an additional connector. The valve and/or additional connector will serve to add more impedance above and beyond what is described by Equations 2-4. Equation 5 governs the impedance of the day tubing:

$$\Delta P_{DT} = a_{DT} Q^2 + b_{DT} Q \quad \text{Eq. 5}$$

The day-tube set is the portion of the system that is used for a surgical day for more than one surgery. The day-tube set is generally used outside of the sterile zone in the operating room. A second tube set, e.g., a patient-tube set, is connected to the distal end of the day-tube for each procedure and completes the tubing to the sterile zone and to the cannula. The patient-tube set and/or day-tube set can contain a backflow preventer, such as a check valve, in order to limit contamination of the day-tube). Equation 5 is used to calculate pressure drops from the day tube set (and patient tube set) if provided. When used with a day-tube set, the fluid flow return path from the patient would be from the patient tube set to a waste receptacle, bypassing the day-tube set and the cassette.

The pressure loss calculated with Equation 5 is added to the pressure loss from Equations 2-4. Equations 1-5 are variations of the general equation for pressure drop for liquid flow in a pipe. The pressure drop is due to friction and is governed by a second order polynomial as long as the geometry is a constant and the incompressible fluid flow remains free of cavitation at a given temperature and pressure.

Figure 4:
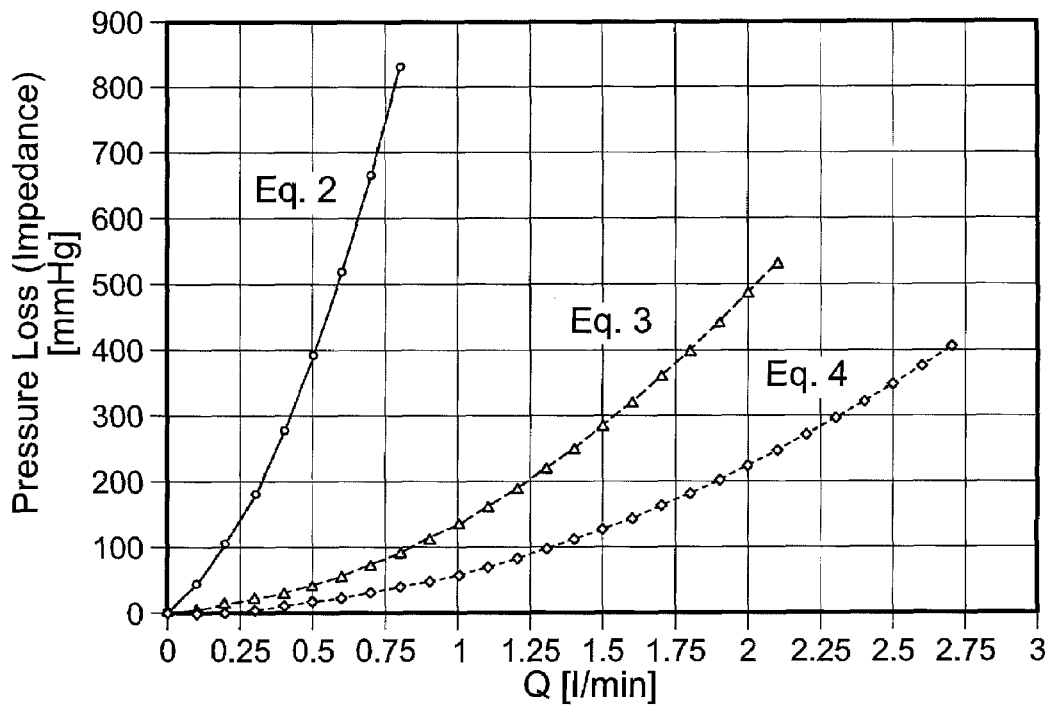
FIG. 4 is a graphical view of pressure losses versus flow rate associated with exemplary arthroscopic instrument sets.
Figure 5:
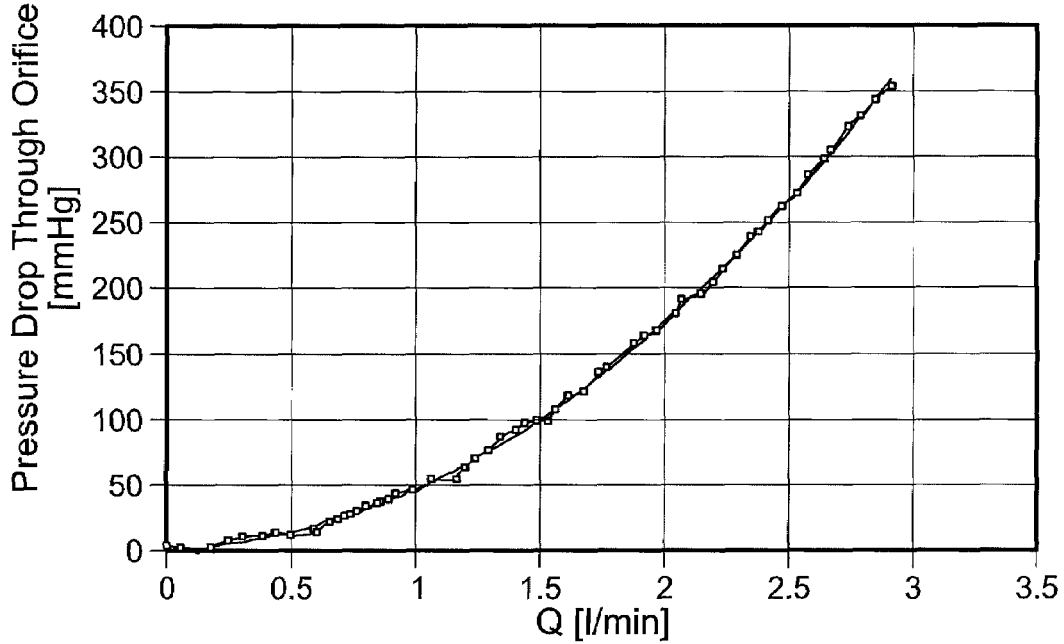
FIG. 5 is a graphical view of a relationship between pressure drop versus flow rate across an orifice.

Referring to FIG. 4, pressure impedance curves are provided for each of the instrument configuration types defined by Equations 2-4. After the impedance values for an instrument configuration are calculated and stored within the control unit 200, the instrument impedance can be selected by the user through the graphical user interface 281 to automatically incorporate a known instrument impedance into any system monitoring performed by the control unit. For example, referring to FIG. 2a, a user may select a large diameter (high flow) instrument configuration, a standard (medium flow) instrument configuration, or a small joint (low flow) instrument configuration.

The flow rate to the joint can be calculated using the relationship between the flow rate (Q) and pressure drop ($\Delta P_o$) across the orifice 370, and the measured pressure reading P1, P2. The pressure drop across the orifice 370 ($\Delta P_O$) is:

$$\Delta P_O = P_1 - P_2 \quad \text{Eq. 6}$$

Similar to Equations 1-5, a fluid flow through a restriction can be represented by a second order polynomial relationship between the rate of flow and pressure drop as follows:

$$\Delta P_O = a_O Q^2 + b_O Q \quad \text{Eq. 7}$$

The flow coefficients of Eq. 7 relative to the restriction 370 can also be derived empirically and for a measured pressure drop value $\Delta P_O$. Equation 7 is then solved for Q as follows with Equation 8:

$$Q = (-b_O \pm \sqrt{(b^2{}_O + 4a_O \Delta P)})/2a_O \quad \text{Eq. 8}$$

The calculated Q value is then inserted into Eq. 1 to solve for $\Delta P_R$, the pressure drop in the instrumentation. Alternatively, the second order polynomial functions described by Equations 1-5 and Equations 7-8 can be written as power functions in the general form of $\Delta P = aQ^b$. The power function equation can then be solved for Q. The value of $\Delta P_R$ is the pressure drop between the measured pressure value of $P_2$ and the distal end of the cannula, i.e. the joint cavity. Then, $$P_J = P_2 - \Delta P_R \quad \text{Eq. 9}$$

The estimated pressure $P_J$ in the joint calculated using equation 9 is used by the control unit 200 to monitor and adjust the pump speed (RPM of an impeller of pump 308) until $P_J$ is equal to $P_{SP}$ (user input set pressure). For example, if $P_J$ is determined to be less than $P_{SP}$, the control unit 200 increases pump speed. If $P_J$ is greater than $P_{SP}$, the control unit 200 decreases pump speed, and if $P_J$ is substantially equal to $P_{SP}$, the control unit maintains pump speed.

Alternatively, or in addition, the control unit can monitor or obtain an additional relationship between, for example, the pump speed (impeller RPM), pressure $P_2$ and flow rate Q to improve system response with closed-loop feedback control. Accordingly, the control unit 200 can monitor or control $P_2$, Q, and RPM based on a three-dimensional system model RPM=f($P_2$, Q).

Figure 6:
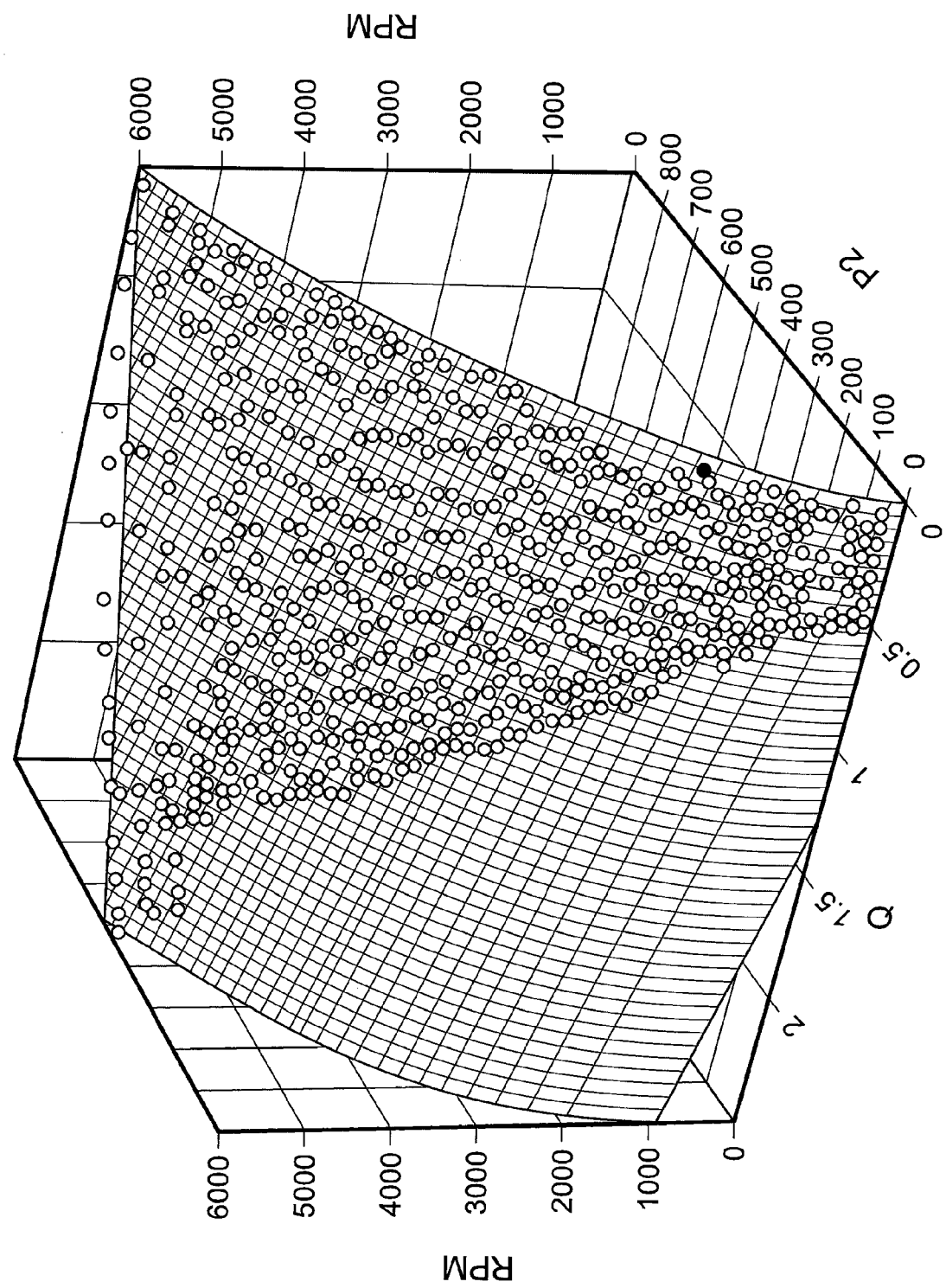
FIG. 6 is a graphical view of a three-dimensional transfer function of flow rate versus flow restriction outlet pressure and pump speed.

Referring to FIG. 6, for example, a three-dimensional model is generated that describes pump RPM as a function of the pressure downstream from the pump ($P_2$) and as a function of the flow rate produced by the pump Q in the form of RPM=f($P_2$, Q). In three-dimensional space, the resulting transfer function S describes a smooth, but fairly intricate surface. The surface function S is derived from empirical data and there are a number of different continuous functions that can be generated, fully describing the surface with varying levels of accuracy. One of these equations is:

$$RPM = a_{RPM} + b_{RPM} \sqrt{P_2} + c_{RPM} Q \qquad \text{Eq. 10}$$

The coefficients of Eq. 10 are empirically derived. FIG. 6 shows the surface that is described by Eq. 10. The joint pressure $P_J$ is estimated based on a knowledge of flow dependent differential pressure across a flow restriction while maintaining smooth and stable distension of the joint. In addition, the response time to variations from the set joint pressure $P_{SP}$ is also fast and reliable.

Figure 7:
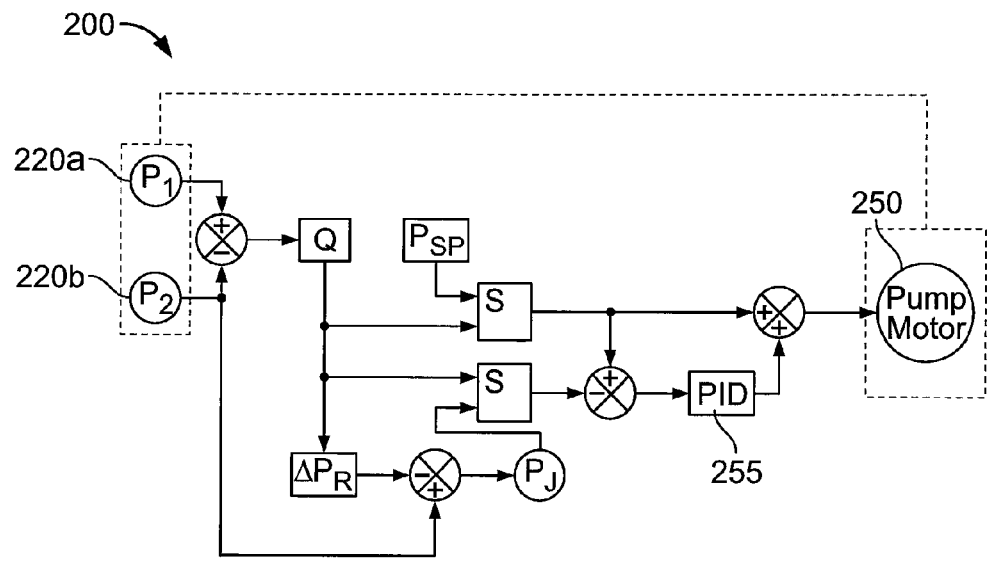
FIG. 7 is a functional block diagram of a control system for the fluid management system based on differential pressure, flow rate and pump speed.

Referring to FIG. 7, an exemplary control process determines joint cavity pressure $P_J$ pressure measurements $P_1$ (Pressure at transducer upstream of orifice) and $P_2$ (Pressure at transducer downstream of orifice) as discussed above, and the process uses the difference between $P_J$ and $P_{SP}$ to control pump speed. The user or control unit 200 sets a target pressure $P_{SP}$ that is input together with the calculated flow rate Q to a transfer function S. The transfer function can be set within the control unit as Equation 11, which represents the smooth surface of FIG. 6. The calculated $P_J$ (joint pressure) is input to the transfer function S along with calculated flow rate Q. The outputs from the transfer function S based on $P_J$ (Joint pressure) and $P_{SP}$ (set pressure) represent two pump RPM values. These values are compared and a proportional-integral-derivative (PID) controller 255 within the control unit 200 is used to provide closed loop feedback to vary actual pump RPM through the pump motor 250 until $P_J$ (Joint pressure) equals or is maintained at $P_{SP}$ (set pressure).

The process of FIG. 7 is performed by a processor within the control unit 200. The control unit can include a processor, such as a CPU or microprocessor, with the PID controller 255 being a component of the processor providing closed loop feedback control. The processor includes logic circuitry that responds to and processes the basic operating instructions and software provided in the control unit and any memory device (s) connected to or within the control unit.

The control unit 200 is also capable of automatically sensing the fluid bag height above the control unit 200 and can give the user a visual and/or audible alarm if the height is insufficient. For example, at zero impeller velocity and zero flow rate, there are no losses through the pump impeller and the orifice, and the measured pressure roughly equals the head height. The control unit 200 therefore can provide a visual and/or audible alarm to the user, such as through the graphical user interface 281 during an initial setup screen or calibration sequence selected by the user.

Alternatively, or in addition, the control unit 200 is capable of automatically sensing the presence of air in the tube sets and can provide the user a visual and/or audible alarm to exchange the empty bag with a full bag. For example, a centrifugal pump may be unable to build up sufficient pressure if air entrained in the system. Therefore, if the control unit 200 detects that the system parameters deviate from the surface of FIG. 6 for a given RPM, i.e., the flow rate and pressure are less than expected, the control unit 200 can provide an indication to the user that air is likely in the tube set.

The control unit 200 can be configured to automatically sense the flow impedance of any instrument set and/or automatically adjust the compensation parameters as explained by Equations 1-5. By automatically detecting the type of instrument configuration, the system is able to dynamically generate multiple impedance curves, e.g., similar to FIG. 4. Accordingly, the control unit 200 can include a self-calibration function to determine background pressure drops associated with existing tube sets and instrument configurations to predict the pressure drop in use.

In addition, or in the alternative, a venturi-type of flow meter can be used instead of an orifice as described above. In a venturi flow meter, fluid passing through a smoothly varying constriction experiences a consistent pressure drop which can be measured and then converted to flow rate. In this case, Equation 6 applies as follows:

$$\Delta P_V = P_1 - P_2 \qquad \text{Eq. 11}$$

$P_2$ is measured at the smallest section of the flow constriction.

Referring to FIGS. 8-11, the pump cassette 300 includes a housing 301 defining a pump chamber 303 which contains a centrifugal pump 308. The pump 308 includes a pump impeller 309, a pump inlet 313, and a pump outlet 314. The inlet 313 is operatively connected to the surgical supply tubing 31 through the inlet tubing connection 397. The outlet 314 is operatively connected to the surgical site through the outlet tubing connection 396. Housing 301 defines a fluid path 397a extending from connection 397 to pump 308 and a fluid path 396a extending from pump 308 to connection 396. Alternatively, the fluid paths 396a, 397a can be defined or partially defined by tubing within the housing extending from connection 397 to pump 308 and from pump 308 to connection 396. Along the fluid path 396a between the pump outlet 314 and the outlet connection 396 is a flow restriction 370, such as an orifice plate or venturi tube. Within or partially defined by housing 301 is a waste fluid return line 399a. Waste fluid returning from the surgical site flows through tubing (not shown) to an inlet tubing connection 395 of the pump cassette 300, to fluid return line 399a, and out outlet tubing connection 398 operatively connected to a waste collection bag or container (not shown). The fluid return line 399a has a U-shaped section 399 of surgical tubing for purposes discussed below. The housing is preferably molded from plastic and intended for single or day use.

Referring to FIGS. 1A-B and 8-15, the cassette slot 210 includes a latch slot 240 for receiving a latch 322 provided on the pump cassette 300, and a pair of contoured tracks 205 with which protrusions on the cassette, discussed below, align as the cassette is inserted into the slot 210. The control unit 200 includes a pump motor 250 for activating the centrifugal pump 308 of the pump cassette, e.g., through magnetic induction, non-contact activation of the pump impeller 309. The pump motor 250 creates a magnetic field that operatively induces the pump impeller 309 to move in response thereto, e.g., the pump impeller 309 can include magnetic pickups that react to the magnetic field of the pump motor 250. In addition, the magnets (not shown) associated with the pump motor 250 and impeller 309 can provide an attractive force that assists in locking or biasing the cassette within the cassette slot 210.

The pump control unit 200 includes the pair of pressure transducers 220a, 220b for measuring respective pressures $P_1$, $P_2$ across the flow restriction 370, a pinch valve 225 to control a flow of fluid returning from the joint cavity 10 and microswitches 230 for operatively engaging with a rear surface 305 of the pump cassette 300 to detect pump cassette type and to detect an operative connection with a properly inserted pump cassette 300.

The pinch valve 225 operatively engages with the U-shaped section 399 of surgical tubing to control the flow of waste fluid leaving the joint cavity 10. For example, the pinch valve 225 is activated to oscillate, e.g., in a reciprocating or lateral motion, to cyclically apply and release a restricting action to the U-shaped section of surgical tubing 399. The cyclical application of the restricting force to the U-shaped section 399 prevents clogging and buildup of coagulated fluid and debris evacuated from the joint cavity 10. In addition, the pinch valve 225 permits the controlled reduction of fluid flow from the joint cavity 10.

In addition, as described with respect to FIG. 7, the control unit 200 includes a processor provided with operating instructions to store empirically obtained and/or calculated pressure drops (impedance values) across a wide range of arthroscopic instruments, e.g., such as various sizes and types of cannula and arthroscopes, and tubing configurations that may be repeatedly used with the system 100. In addition, the control unit includes software or logic circuitry capable of processing control algorithms to control pump speed and joint pressure, such as Equation 11 described above.

Referring to FIGS. 1A-B and 8-15, the generally rectangular shaped pump cassette housing 301 includes an upper end 301a, a lower end 301b, a distal end 301c and a proximal end 301d. The upper and lower ends 301a, 301b each includes a pair of raised protrusions 310, 311, a pair of relatively higher raised protrusions 315, 316, and a pair of trapezoidally shaped protrusions 320, 321, which are received in the track 205 of the cassette slot 210. The distal end 301c defines a cassette type recognition slot 325 and a cassette insertion recognition recess 330, which together with microswitches 230 enable the system to recognize the type of cassette that has been inserted and to recognize that a cassette has been inserted. The distal end 301c also defines a pinch valve cutout 340, which exposes an area of the U-shaped surgical tubing portion 399 to the pinch valve unit 225.

Figure 11:
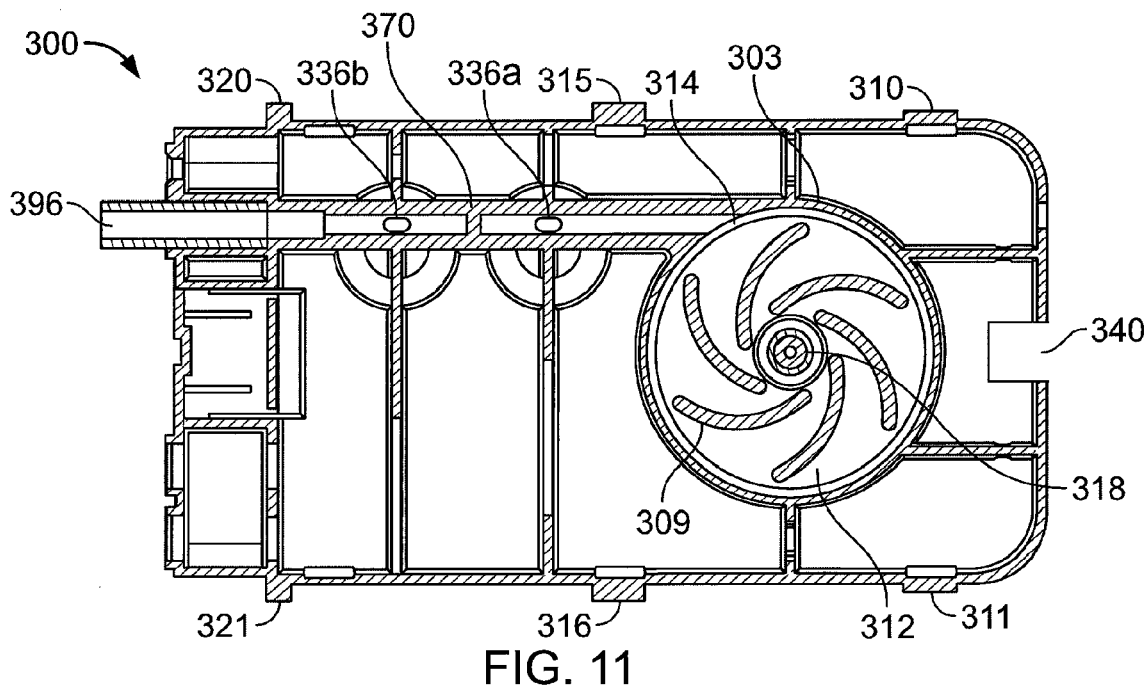
FIG. 11 is a side sectional view of a pump cassette taken with respect to line A-A of FIG. 9 and FIG. 10.
Figure 12:
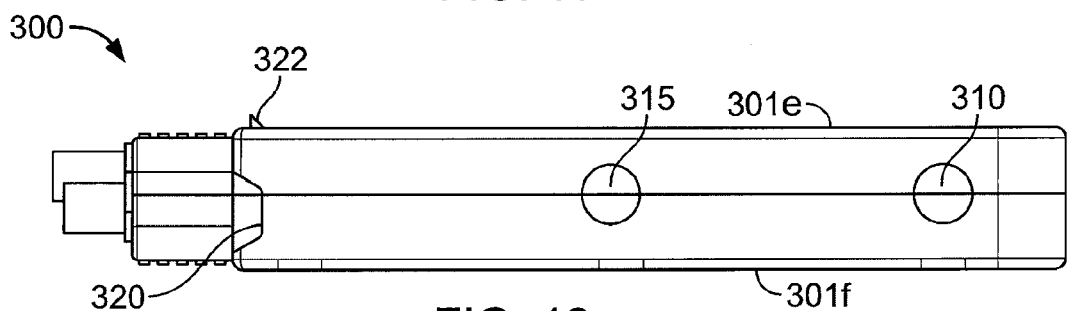
FIG. 12 is an upper side view of the pump cassette of FIG. 9.
Figure 13:
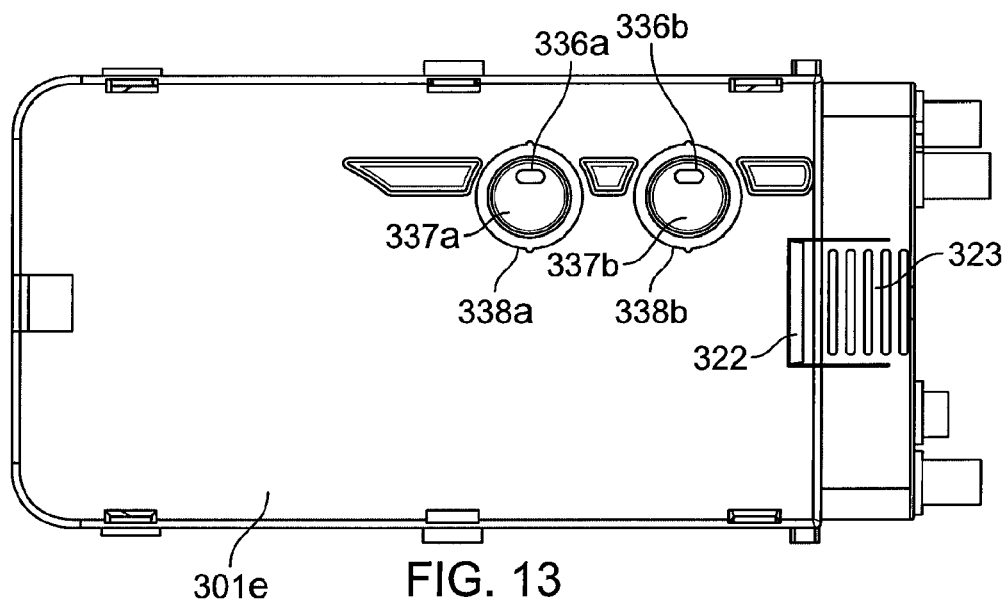
FIG. 13 is a rear side view of the pump cassette of FIG. 9.
Figure 14:
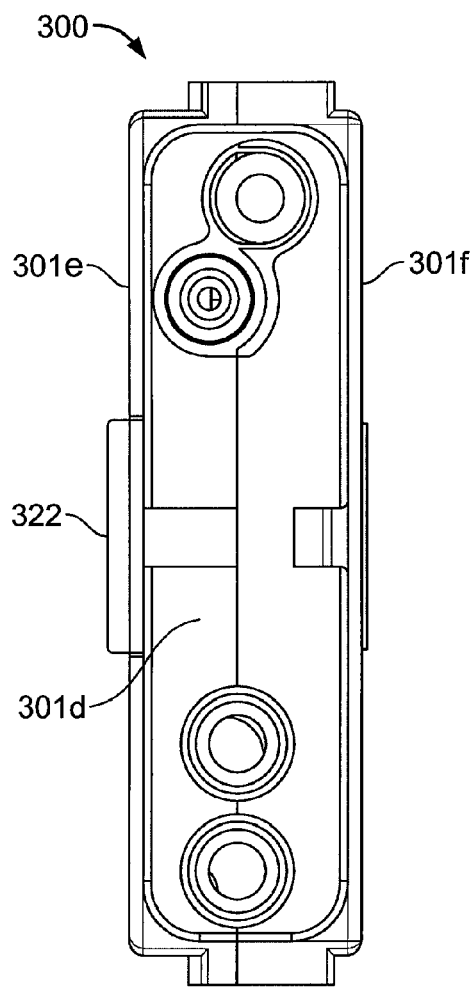
FIG. 14 is a front end view of the pump cassette of FIG. 9.
Figure 15:
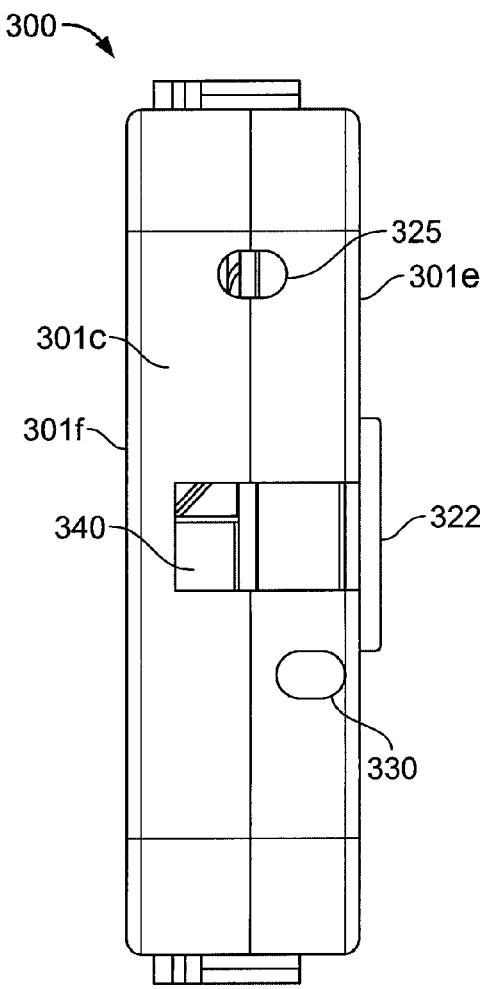
FIG. 15 is a rear end view of the pump cassette of FIG. 9.

Referring to FIG. 11, the flow restriction orifice 370 is provided between the pump outlet 314 and the pump outlet tubing connection 396, and is also positioned between a pair of pressure transducer ports 336a, 336b by which pressure transducers 220a, 220b within the control unit 200 sense pressure readings P1, P2, respectively.

Referring to FIGS. 12-15, the pump cassette includes an inner surface 301e that engages with the cassette slot 210 and an outer surface 301f that faces away from the control unit 200 when the cassette 300 is mounted within the cassette slot 210. The inner surface 301e includes a pair of pressure membranes 337a, 337b that cover the respective pressure transducer ports 336a, 336b. The pressure membranes 337a,337b are flexible membranes that provide a fluid-tight seal over the respective pressure transducer ports 336a, 336b and permit the transmission of pressure readings to the pressure transducers 220a, 220b, respectively of the control unit 200. In order to prevent damage or wear to the pressure membranes 337a, 337b and a relatively smooth profile to the inner surface 301e, the membranes are provided within an annular groove 338a, 338b countersunk into the inner surface 301e of the cassette housing 301. The inner surface 301e is also provided with a latch 322 which operatively engages the latch slot 240 formed in the cassette slot 210 of the control unit 200. The latch 322 permits the user of the control unit to release the cassette 300 from engagement with the control unit 200 by pressing or squeezing a tab 323 of the latch 322.

Figure 16:
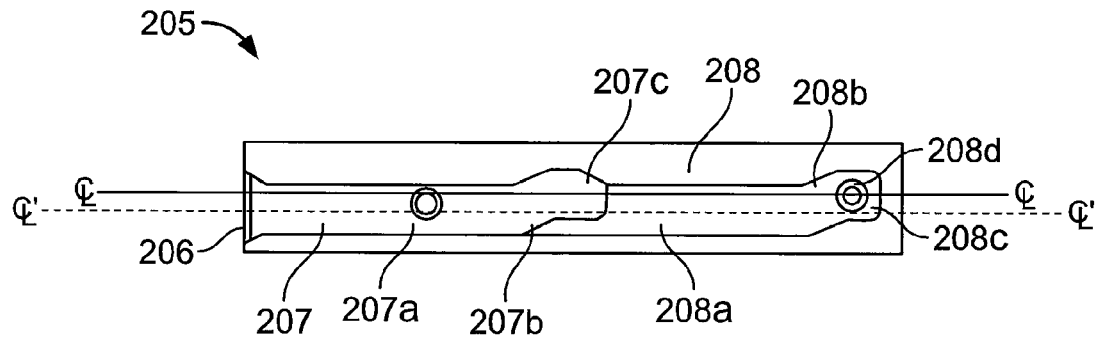
FIG. 16 is a plan view of an exemplary guide track for a pump control unit.
Figure 17:
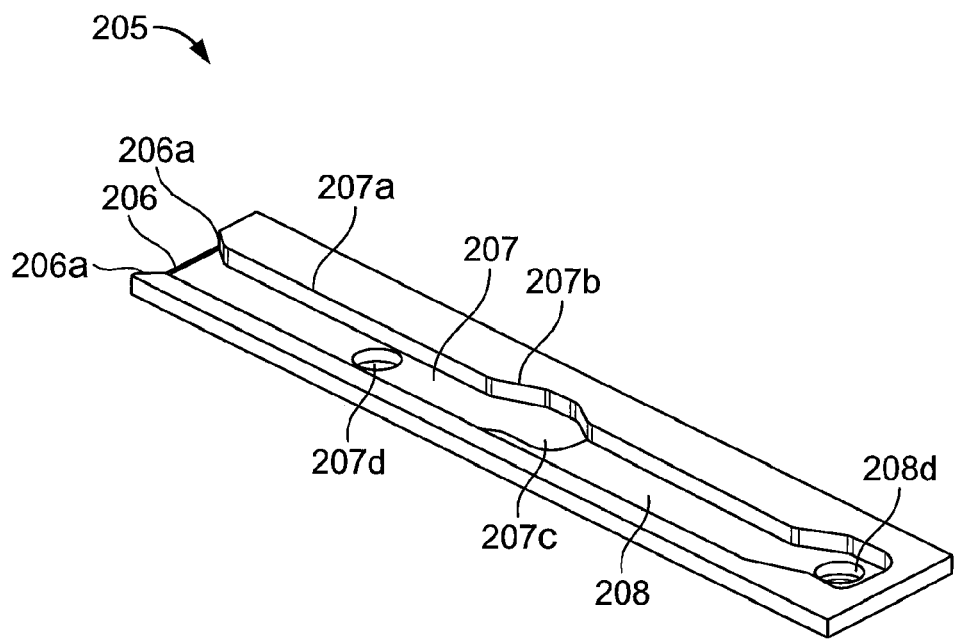
FIG. 17 is perspective view of the guide track of FIG. 16.

Referring to FIGS. 1A, 1B, and 8-17, the protrusions 310, 311, 315, 316, 320, 321 align with guide tracks 205. Referring to FIGS. 16 and 17, the guide tracks 205 each include a trapezoidally shaped first guide track section 206, a second guide section 207 and a third guide section 208. The trapezoidally shaped first guide track section 206 is a relatively deep groove that is shaped to permit the easy insertion of the distal end 301c of the cassette 300 into the cassette slot 210. In addition, the trapezoidally shaped first guide track section 206 includes interior edges 206a shaped to substantially conform to the exterior surfaces of the trapezoidally shaped protrusions 320, 321 formed nearest the proximal end 301d of the cassette 300. Accordingly, the trapezoidally shaped first guide track section 206 acts as a stop against the insertion of the trapezoidally shaped protrusions 320, 321 beyond a predetermined distance into the cassette slot 210.

The second guide track section 207 includes a linear track section 207a transitioning into an angled track section 207b and ending in an end portion 207c. The linear track section 207a also defines a recess 207d that is used to insert a fastener to secure the track section 207 to the cassette slot 210. The third guide track section 208 includes a linear track section 208a transitioning into an angled track section 208b and ending in an end portion 208c. The linear track section 208a also defines a recess 208d that is used to insert a fastener to secure the track section 208 to the cassette slot 210. The trapezoidally shaped first guide track section 206 and the second guide track section 207 are relatively deeper grooves than the third guide track section 208 that is sized to receive the relatively smaller protrusions 310, 311. The trapezoidally shaped track section 206 is formed off-center with respect to an axial centerline passing approximately through the geometric centers of the second and third track end portions 207b, 208b.

Referring to FIGS. 18-23, the offset center of the trapezoidally shaped track section 206 with respect to the end portions 207c, 208c facilitates the insertion of the pump cassette 300 into the slot 210 with minimal friction between the inner surface 301e and the opposing surface of the slot 210. In addition, the flexible membranes 337a, 337b are protected against wear and tear as the pump cassette 300 is eased into the guide track 205 and eventually brought into contact with a mating surface of the cassette slot 210 and in alignment with the pressure transducers 220a, 220b of the control unit 200.

Figure 18:
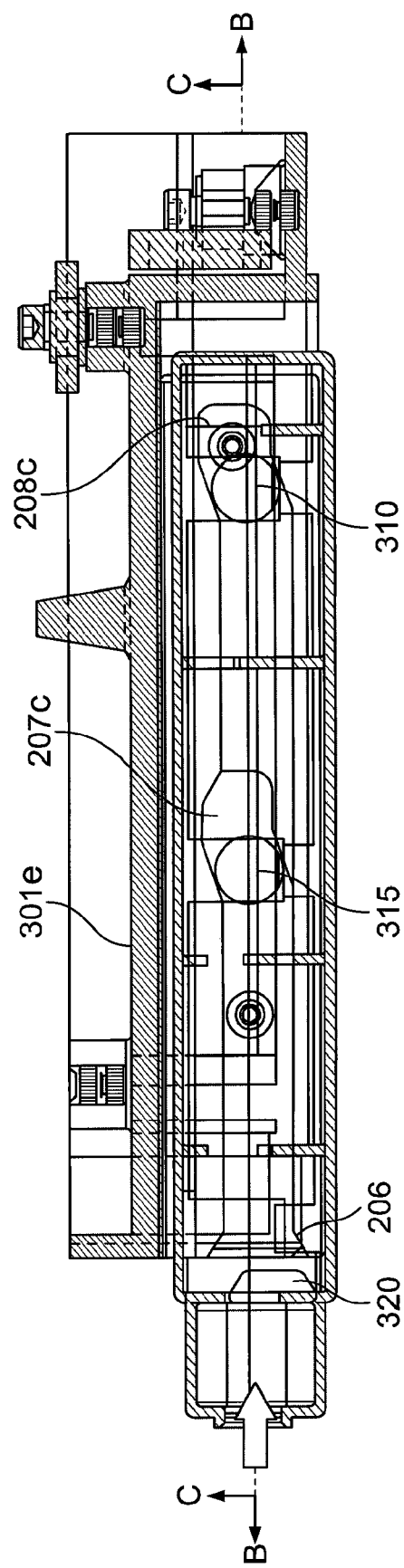
FIG. 18 is a partial, lower sectional view of the pump cassette partially inserted into a cassette slot within the pump control unit.
Figure 19:
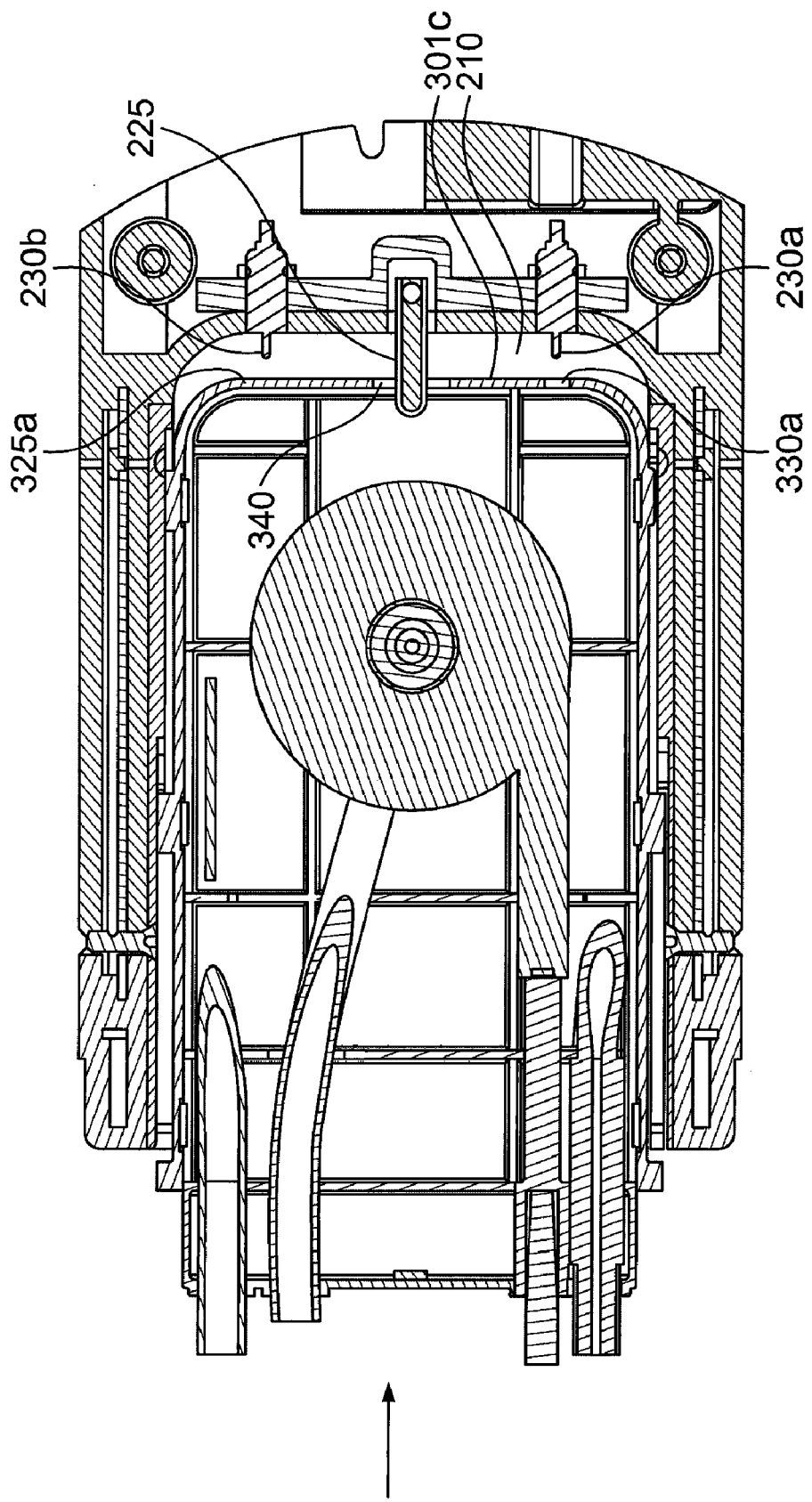
FIG. 19 is a sectional view of the pump cassette and cassette slot taken along line B-B of FIG. 18.
Figure 20:
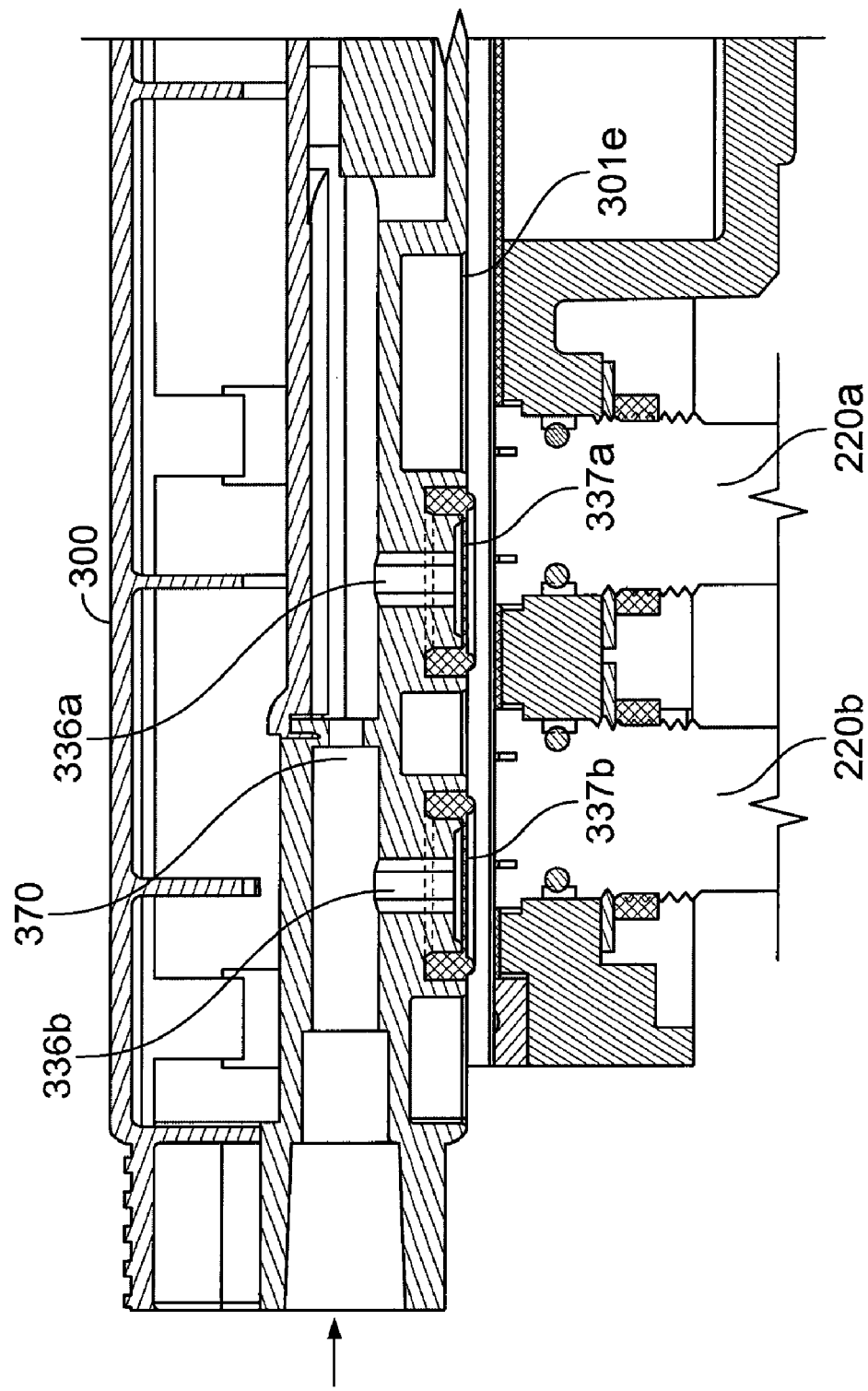
FIG. 20 is partial, lower sectional view of the pump cassette partially inserted into the cassette slot taken along line C-C of FIG. 18.

Referring to FIGS. 18-20, the cassette 300 is shown in a partially inserted position with respect to the cassette slot 210. As the cassette 300 is inserted into the cassette slot 210, the pinch valve 225 is aligned with the pinch valve cutout 340 on the pump cassette 300. In addition, the leading end of microswitch 230a is aligned with cassette insertion recognition recess 330. The leading end of microswitch 230b is axially aligned with cassette type recognition through slot 325.

Figure 21:
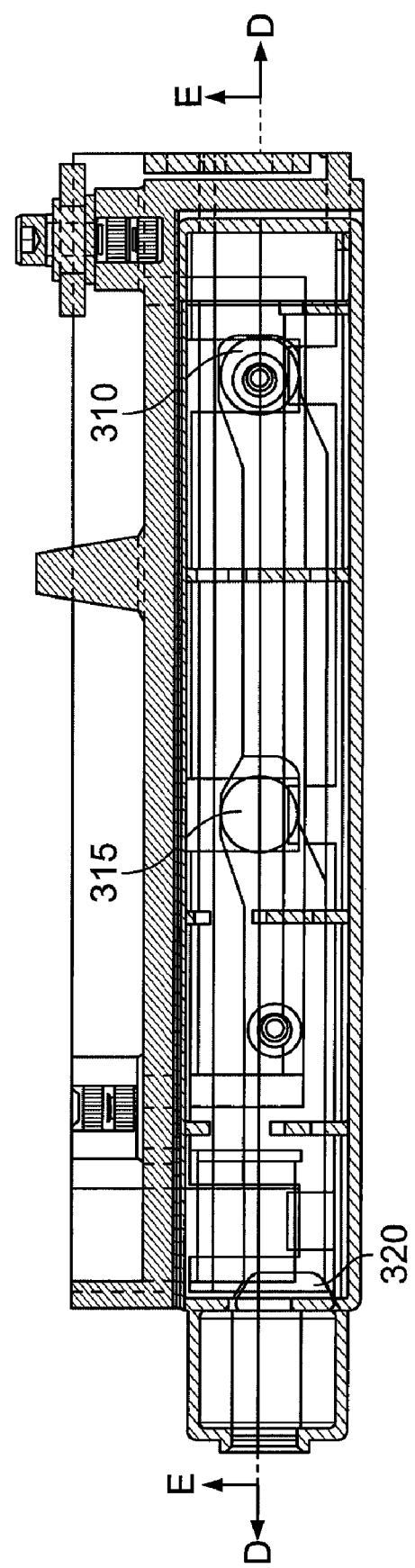
FIG. 21 is a partial, lower sectional view of the pump cassette fully inserted into the cassette slot within the pump control unit.
Figure 22:
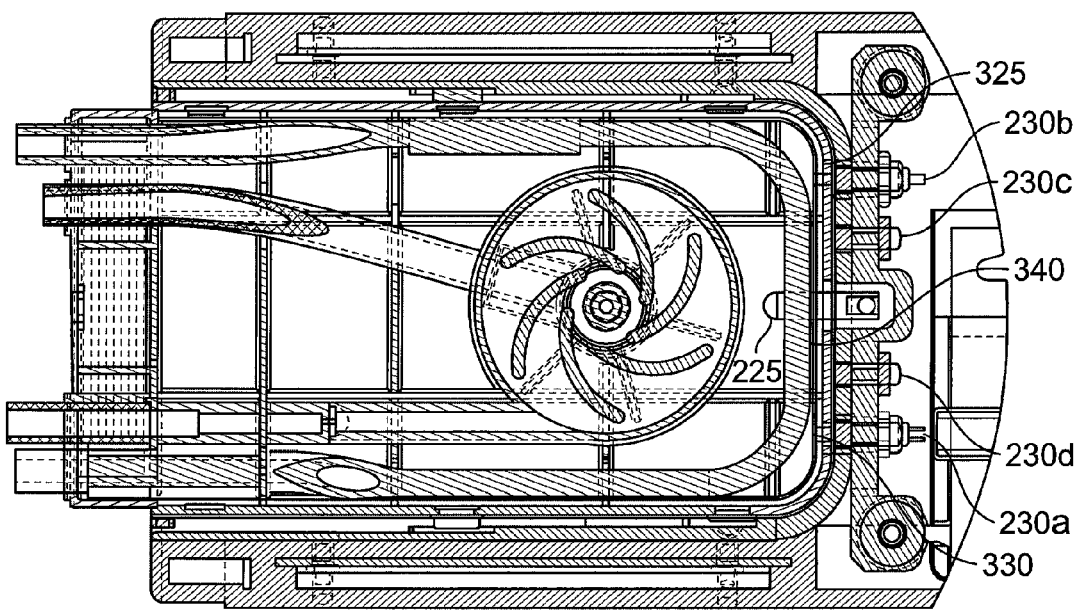
FIG. 22 is a sectional view of the pump cassette and cassette slot taken along line D-D of FIG. 21.
Figure 23:
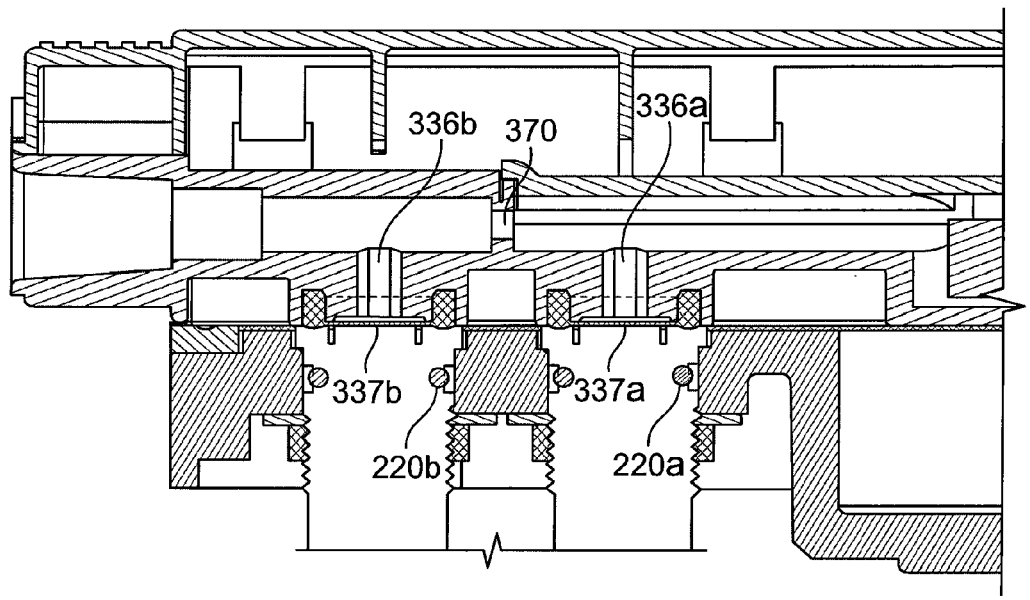
FIG. 23 is partial, lower sectional view of the pump cassette and cassette slot taken along line E-E of FIG. 21.

Referring to FIGS. 21-23, the remaining microswitches 230c, 230d are not aligned with corresponding slots or recesses and therefore generate a signal as the leading ends are compressed against the distal end 301c of the cassette 300 being inserted into the slot 210. Accordingly, various pump cassette types can be provided with unique slot and recess configurations that permit a control unit 200 to recognize the cassette type and/or the insertion of a cassette within the slot 210. Although four microswitches 230 are shown, any number of microswitches can be provided to support the recognition and engagement with a variety of pump cassette types.

Figure 24:
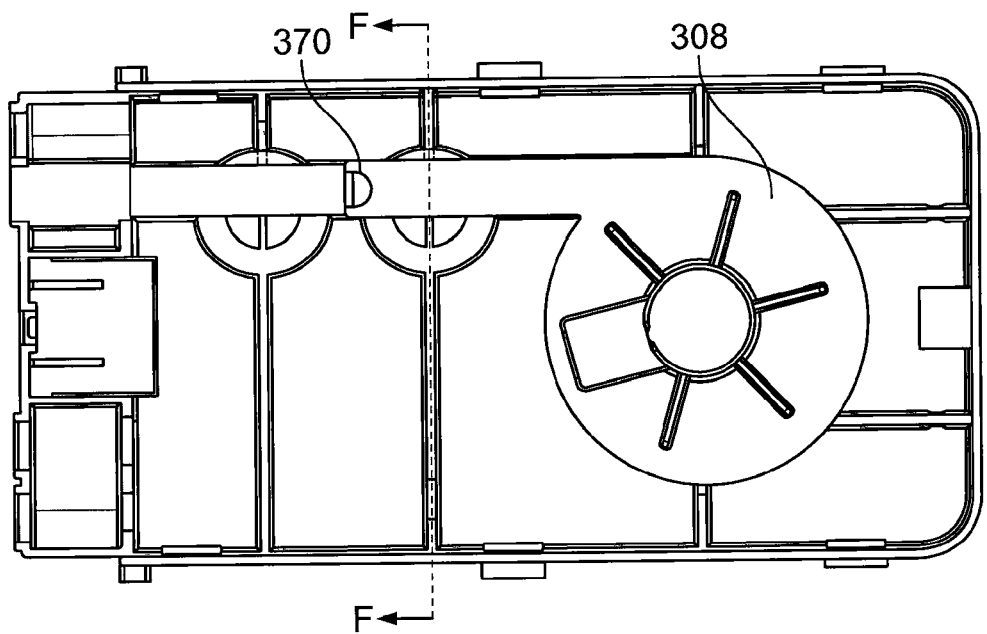
FIG. 24 is side view of a pump cassette housing and cap.

Other embodiments are within the scope of the following claims. For example, referring to FIGS. 24-26, the orifice 370 includes a cap 378 that is welded along a lower surface 375 thereof to an opening within the cassette housing 301, above a lower half 370a of the orifice 370 and downstream from the pump outlet 314. The cap 378 is inserted over the lower half 370a of the orifice 370 and laser welded to form a closed chamber with relatively little or no machining or complicated molding steps required during the manufacture of the housing 301. The cap 378 and the lower half 370a together form an orifice 370 of generally circular cross-section that permits the formation of the orifice 370 with relatively uncomplicated molding or manufacturing steps. The use of a cap welded to the housing 301 can also be used to manufacture other flow restrictions, such as a venturi-type flow restriction, instead of the orifice 370. Alternatively, or in addition, the housing 301 and the cap 378 could be bonded together by other processes such as sonic welding, chemical bonding or mechanical fastening.

Figure 8:
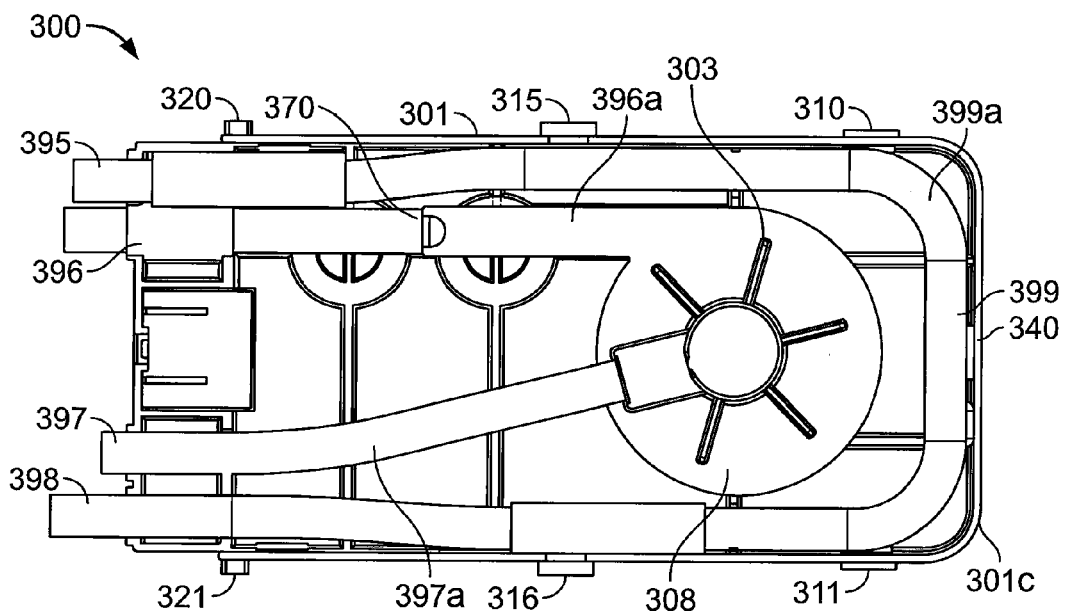
FIG. 8 illustrates the pump cassette of FIG. 1B with a housing member removed.
Figure 9:
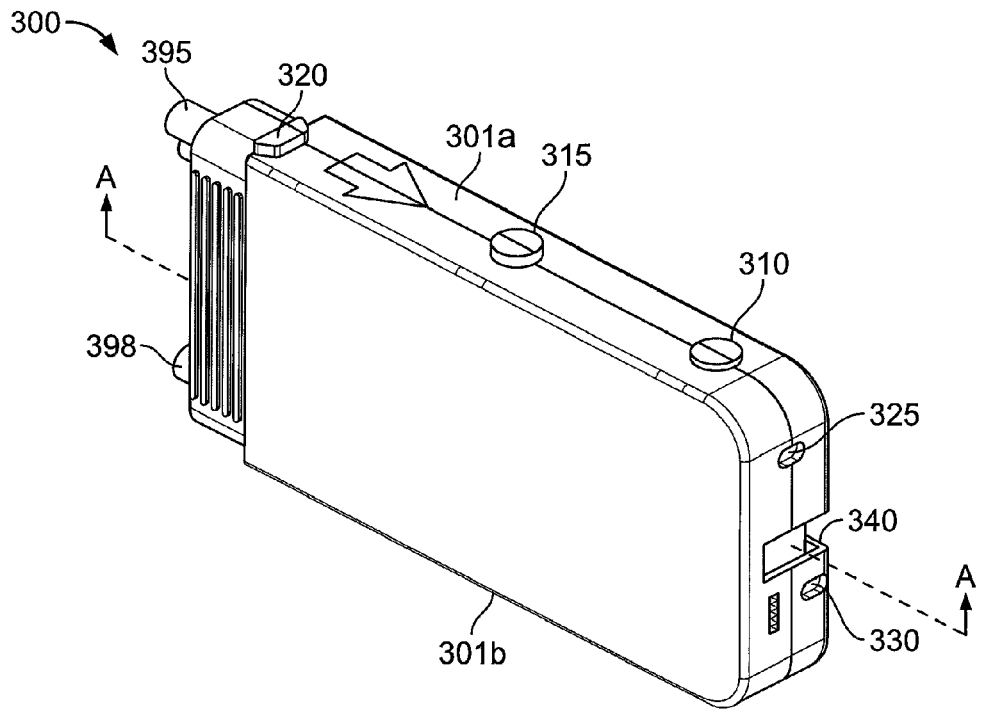
FIG. 9 is a perspective view of the pump cassette.
Figure 10:
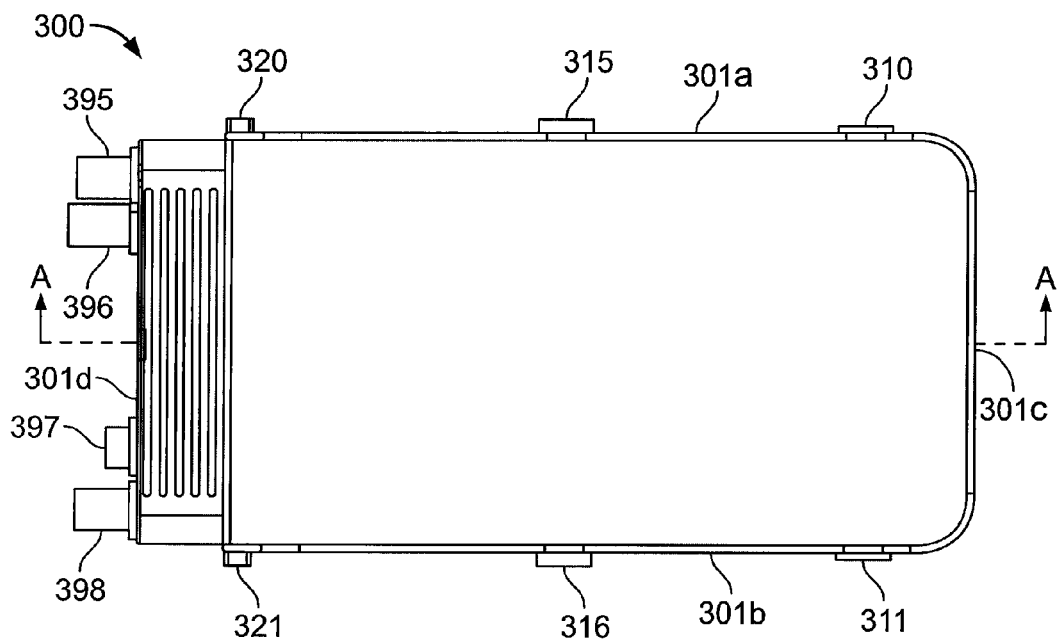
FIG. 10 is a side view of the pump cassette of FIG. 9.
Figure 25:
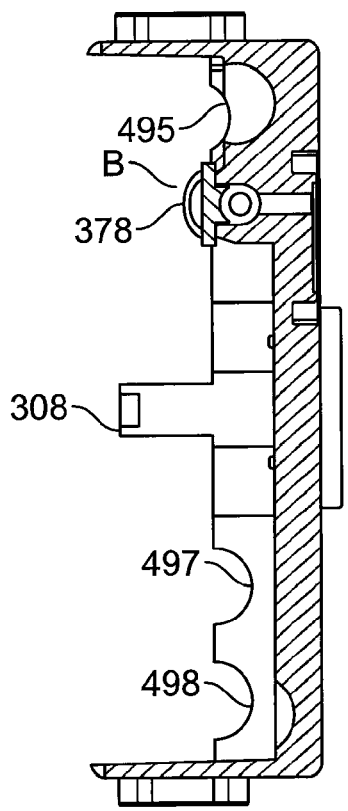
FIG. 25 is a sectional view taken along line F-F in the pump cassette housing of FIG. 24.
Figure 26:
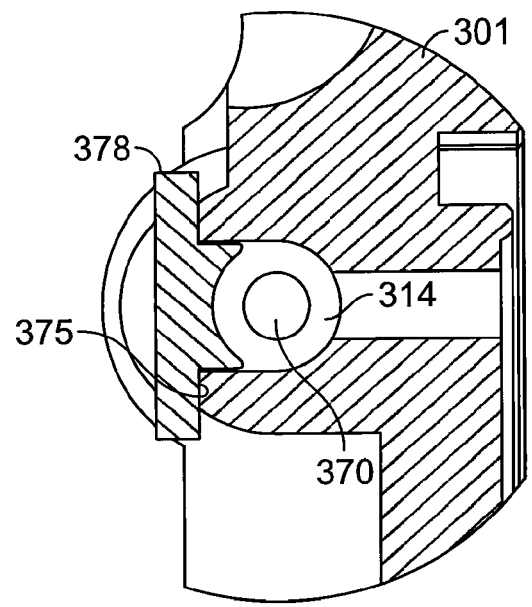
FIG. 26 is an enlarged view of region B of FIG. 25.

Referring to FIG. 25, the housing 301 can also define surgical tubing grooves 495, 497, 498 that facilitate the insertion of surgical tubing within the housing 301 to form the conduits shown in FIG. 8.

Referring to FIGS. 1A, 1B and 16 and 17, loading and latching of the cassette to the side of the control unit is easy for the user, and rigid. The track 205 and the cassette 300 are designed in such a way that the cassette can be inserted in only one orientation with respect to the slot 210. However, the track 205 and cassette 300 can be configured to permit more than one orientation as long as pressure transducers 220a, 220b are aligned with the corresponding membranes 337a, 337b on the cassette 300.

The protrusions 310, 315 may be generally circular in shape or may include alternative geometric profiles such as rectangular, square and/or may be formed of relatively the same size to correspond with equally deep guide track 205 sections. One or more of the protrusions and guide tracks may be axially aligned and/or off-center to provide various insertion paths for the cassette 300. Although the tracks 205 shown permit the insertion of the cassette 300 at a right angle with respect to the front of the control unit, while keeping the soft pressure transfer membranes 337a, 337b located on the inner side 301e of the cassette 300 at a predetermined safe distance from the side of the control unit 200, the tracks 205 may be constructed of relatively linear alignment tracks if the membranes are sufficiently durable to withstand rubbing against the cassette slot 210.

The latch 322 on the inner side 301e of the cassette 300 automatically snaps into a mating slot 240 (FIG. 1A) on the side of the control unit 200 to keep the cassette 300 firmly in place. However, more than one latch 322 in various locations may be provided to securely fasten the cassette 300 within the slot.

Each pressure transducer 220a, 220b can be provided with a load cell that measures a force exerted thereon by the corresponding membrane 337a, 337b of the cassette 300. The force exerted by the membranes 337a, 337b is converted into a pressure reading by dividing the applied force by the area of contact between the membranes 337a, 337b and the load cell (Pressure=Force/Area). The pressure transducers are mechanically robust, resistant to physical damage, and/or protected from wear and tear by the alignment tracks 205.

With respect to the pinch valve 225, as the cassette 300 is inserted the slot 210, the exposed tubing of the U-shaped tube section 399 slides into place such that the tubing can be pinched by the pinch valve 225. The pinch valve 225 controls the rate of outflow from the joint 10 and pulsates back and forth from a nominal set position in order to limit tissue clogging and fluid flow leaving the joint 10. The pulsating action of the pinch valve 225 is controlled by a certain amplitude and frequency that is tuned for the system and/or each pump cassette type. For example, an exemplary pinch valve 225 can employ an amplitude of about 0.05 inches, and a frequency of about 1.1 Hz. As any fluid or resected tissue is aspirated or evacuated from the joint cavity 10, the fluid and tissue is prevented from building up by the pulsating action of the pinch valve 225. The oscillation of the pinch valve 225 creates a continuous compression and relaxation of the tube that limits tissue build-up and eventual clogging.

In addition, or in the alternative, a pinch valve position may be controlled from a preset minimum to a preset maximum through a proportional device such as a linear actuator. However, the amount of flow passing through the pinched tube is governed by a non-linear relationship with respect to flow area inside the tube. For example, the flow rate passing near the pinch valve 225 (or out of the joint 10) can be described as a function of area, i.e. $Q_O$=f(Area). Since area is a function of linear position of the pinch valve, i.e. Area=f(x) where x is the distance traveled by the pinch valve from a predetermined zero position, flow rate is a function of pinch valve position and can be written as $Q_O$=f(x). Equation 12 describes this relationship as a multi-order polynomial, e.g., a third order polynomial.

$$Q_O = ax^3 + bx^2 + cx + d \qquad \text{Eq. 12}$$

The respective coefficients of Equation 12 can also be derived empirically and the values set within the control unit 200 or determined during an initial calibration procedure of the control unit 200. Accordingly, simple linearly graduated controls, such as a setting range of 0-100% of the pinch valve position, can be automatically converted to yield substantially linearly increasing or decreasing outflow rates from the joint cavity 10.

The pinch valve 225 can be used to control the joint pressure, e.g., to control excessive draining of the joint cavity 10. For example, if excessive vacuum level is used to aspirate the joint cavity 107 the pump 308 may produce flow rates at highest capacity and still not be able to attain the target joint pressure. The control unit 200 can be configured to identify a condition where the flow rate is at full capacity and joint pressure is still not attained. In this case, the pinch valve 225 is operated to squeeze the outflow tube more than a typical set position, and temporarily override a set position of the pinch valve 225 to reduce the outflow from the joint cavity 10 until the inflow is able to maintain the target joint pressure.

The distal end 301c of the cassette 300 which is inserted first can be provided with any number of slots and recesses. For example, referring to FIGS. 9 and 15, the cassette 300 is provided with a single recess 325 and anywhere from zero to three slots 330. The control unit 200 is provided with four micro-switches (FIGS. 1A and 19) that align with the presence or absence of slots to recognize the type of cassette and also to recognize whether a cassette is present or not. For example, if there is a slot in the cassette, the micro-switch plunger passes through the slot and is not actuated. If a slot is absent, the micro-switch plunger is depressed and thus is activated. The micro-switch that aligns with the recess gets activated last; so as to make certain that the cassette type is identified prior to the actual recognition of a cassette. Alternatively, the number of microswitches, recesses, and/or slots can be varied to assist in recognizing a large number of pump cassette types. Alternatively, or in addition, the control unit 200 can utilize an external wired or wireless sensor to signal the control unit regarding the presence and type of a cassette. For example, an optical switch or radio frequency identification (RFID) can be used for cassette recognition and type.

The system permits the delivery of fluid to a body cavity at a predetermined set pressure, e.g., in a range of approximately 10-150 mmHg, and independent of flow rate. Pressure can be maintained at a substantially constant level at flow rates ranging from about 0-2.5 L/min and/or works with multiple cannula and arthroscope inflow instrument configurations without requiring manual calibration. The apparatus has a touch panel color display and a user-friendly graphical user interface (GUI). The graphical user interface 281 can provide default and custom settings and/or requires no special set up or calibration procedures. The system can use reusable or disposable pump cassette or tubesets. The system can also regulate outflow from the joint cavity with the use of a pulsating pinch valve to limit clogging.

A number of embodiments have been described. Nevertheless, it will be understood that various modifications may be made. For example, the housing can include flow path conduits of surgical tubing, such as clear, soft and/or relatively rigid PVC surgical tubing. U.S. Pat. No. 5,630,799 (Beiser et al.), which issued May 20, 1997, the entire contents of which is incorporated by reference herein, describes exemplary features of a non-contact centrifugal pump and motor configuration, exemplary pump cassette construction, and exemplary, applicable materials that can be used to construct components of the present fluid management system 100. Although the pump is described as a centrifugal pump, a positive displacement pump, such as a peristaltic pump, could be used in the fluid management system 100. However, if the pump is a positive displacement pump, the control algorithms used to maintain joint pressure and calculate system parameters can be modified for positive displacement pump flow relationships.

Accordingly, other embodiments are within the scope of the following claims.

What is claimed is:

1. A fluid flow device, comprising:
    a housing configured to releasably mate with a surgical control unit for controlling fluid flow during a surgical procedure;
    a fluid path within the housing;
    first and second ports which communicate a fluid pressure within the fluid path to at lest one pressure for measuring fluid pressure within the path;
    a restrictor for restricting fluid flow at a restriction location along the fluid path, the first port being located upstream of the restriction location and the second port being located downstream of the restriction location; and
    a fluid pump within the housing.

2. The fluid flow device of claim 1, wherein the restrictor comprises a region of decreased cross-sectional area along the fluid path.

3. The fluid flow device of claim 1, wherein the ports are openings defined in a wall of the housing.

4. The fluid flow device of claim 1, further comprising a flexible membrane covering the first port and a flexible membrane covering the second port.

5. The fluid flow device of claim 1, wherein the pump comprises a non-contact, magnetic coupling configured to be operatively driven by a motor external to the housing.

6. The fluid flow device of claim 1, further comprising a second fluid path within the housing.

7. The fluid flow device of claim 6, further comprising a valve configured to selectively control fluid flow through the second fluid path.

8. The fluid flow device of claim 1, further comprising the surgical control unit.

9. The fluid flow device according to claim 1, further comprising day-tubing operatively connected to the housing, the day-tubing including a valve for limiting backflow.

10. The fluid flow device of claim 9, wherein the surgical control unit includes a first pressure sensor and a second pressure sensor.

11. The fluid flow device of claim 10, wherein the sensors align with the ports when the housing is mated with the surgical control unit.

12. The fluid flow device of claim 10, wherein the surgical control unit defines a slot for receiving the housing.

13. The fluid flow device of claim 12, wherein the slot includes a guide track and the housing includes one or more protrusions configured to matingly engage the guide track.

14. The fluid flow device of claim 13, wherein the guide track comprises a linear track section and an angled track section.

15. The fluid flow device of claim 8, further comprising a valve configured to impart a pulsating action to a fluid conduit within the housing.

16. The fluid flow device of claim 12, wherein the control unit comprises a processor configured to selectively control pump speed based on a measured pressure drop across the flow restrictor.

17. The fluid flow device of claim 16, wherein the processor is configured to selectively control pump speed based on a calculated flow rate, a setpoint surgical site pressure, and a calculated surgical site pressure.

18. The fluid flow device of claim 17, wherein the processor is operatively connected with a proportional-integral-derivative controller configured to provide closed-loop feedback with respect to a comparison between the setpoint surgical site pressure and the calculated surgical site pressure.

19. The fluid flow device claim 17, wherein the processor is configured to control pump outlet pressure (P2), flow rate (Q) and pump speed (RPM) based on a three-dimensional system model defined by the function RPM=f (P2, Q).

20. The fluid flow device of claim 19, wherein the controller is configured to provide open-loop feed forward control with respect to a comparison between the setpoint surgical site pressure and the calculated surgical site pressure.

21. An apparatus for controlling fluid pressure within a body cavity comprising:
    means for pumping fluid to the body cavity through a flow restrictor located between the body cavity and a fluid pump;
    means for measuring a pressure change across the flow restrictor;
    means for calculating the fluid pressure within the body cavity based on the measured pressure change; and
    means for controlling the fluid flow to the body cavity based on the calculated fluid pressure.

22. A fluid flow device, comprising:
    a housing including at least one protrusion configured to releasably mate with a surgical control unit for controlling fluid flow during a surgical procedure, the at least one protrusion configured to matingly engage a guide track of the surgical control unit;
    a fluid path within the housing;

first and second ports which communicate a fluid pressure within the fluid path to at lest one pressure sensor for measuring fluid pressure within the path;

a restrictor for restricting fluid flow at a restriction location along the fluid path, the first port being located upstream of the restriction location and the second port being located downstream of the restriction location; and a fluid pump within the housing.

23. The fluid flow device of claim 22, further comprising a flexible membrane covering the first port and a flexible membrane covering the second port, wherein the flexible membranes seat on a first pressure sensor and a second pressure sensor of the surgical control unit when the at least one protrusion matingly engages the guide track of the surgical control unit.

24. The fluid flow device of claim 22, wherein the at least one protrusion comprises a first protrusion and a second protrusion, the first protrusion having a first height and the second protrusion having a second height different from the first height.

25. An apparatus for controlling fluid pressure within a body cavity comprising:

a control unit;

a cassette having at least one projection for engaging a guide track of the control unit;

a pump within the cassette for pumping fluid to the body cavity through a flow restrictor located in the cassette;

a sensor located in the control unit which measures a pressure change across the flow restrictor, wherein the control unit is operable to calculate the fluid pressure within the body cavity based on the measured pressure change, and wherein the control unit controls the fluid flow to the body cavity based on the calculated fluid pressure.

* * * * *

UNITED STATES PATENT AND TRADEMARK OFFICE
CERTIFICATE OF CORRECTION

| | | |
|---|---|---|
| PATENT NO. | : 7,604,610 B2 | Page 1 of 1 |
| APPLICATION NO. | : 11/423899 | |
| DATED | : October 20, 2009 | |
| INVENTOR(S) | : Cemal Shener | |

It is certified that error appears in the above-identified patent and that said Letters Patent is hereby corrected as shown below:

Column 12, Line 45, delete "107" and replace with -- 10, --;

Column 13, Line 50, Claim 1, delete "lest" and replace with -- least --;

Column 13, Line 50, Claim 1, after "pressure", insert -- sensor --;

Column 14, Line 42, Claim 19, after "device", insert -- of --; and

Column 15, Line 2, Claim 22, delete "lest" and replace with -- least --.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,604,610 B2 |
| APPLICATION NO. | : 11/423899 |
| DATED | : October 20, 2009 |
| INVENTOR(S) | : Shener et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

Fifth Day of October, 2010

David J. Kappos
*Director of the United States Patent and Trademark Office*